(12) United States Patent
McAuley

(10) Patent No.: US 7,998,095 B2
(45) Date of Patent: *Aug. 16, 2011

(54) OCCLUSION DEVICE

(75) Inventor: Steven A. McAuley, Chanhassen, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1762 days.

This patent is subject to a terminal disclaimer.

(21) Appl. No.: 11/207,235

(22) Filed: Aug. 19, 2005

(65) Prior Publication Data

US 2007/0043337 A1    Feb. 22, 2007

(51) Int. Cl.
*A61N 7/00*    (2006.01)
(52) U.S. Cl. .................. 601/2; 606/41; 606/49; 606/50; 607/101; 607/102; 600/411; 600/439
(58) Field of Classification Search .................. 600/437, 600/439, 411; 601/2; 606/41, 49–50; 607/101–102
See application file for complete search history.

(56) References Cited

U.S. PATENT DOCUMENTS

| | | | |
|---|---|---|---|
| 5,370,675 A * | 12/1994 | Edwards et al. | |
| 5,749,889 A * | 5/1998 | Bacich et al. | |
| 5,769,790 A | 6/1998 | Watkins et al. | |
| 5,919,200 A | 7/1999 | Stambaugh et al. | |
| 5,944,738 A | 8/1999 | Amplatz et al. | |
| 6,007,514 A | 12/1999 | Nita | |
| 6,024,718 A | 2/2000 | Chen et al. | |
| 6,352,503 B1 * | 3/2002 | Matsui et al. | |
| 6,378,501 B1 | 4/2002 | Hisato et al. | |
| 6,458,100 B2 | 10/2002 | Roue et al. | |
| 6,482,224 B1 | 11/2002 | Michler et al. | |
| 6,645,225 B1 | 11/2003 | Atkinson | |
| 6,650,923 B1 | 11/2003 | Lesh et al. | |
| 6,716,184 B2 | 4/2004 | Vaezy et al. | |
| 6,755,790 B2 | 6/2004 | Stewart et al. | |
| 6,776,784 B2 | 8/2004 | Ginn | |
| 7,186,251 B2 * | 3/2007 | Malecki et al. | 606/41 |
| 7,678,133 B2 * | 3/2010 | Modesitt | |
| 2002/0099390 A1 | 7/2002 | Kaplan et al. | |
| 2002/0103459 A1 | 8/2002 | Sparks et al. | |
| 2002/0107531 A1 | 8/2002 | Schreck et al. | |

(Continued)

FOREIGN PATENT DOCUMENTS

WO        9713463        4/1997

(Continued)

OTHER PUBLICATIONS

International Search Report, Dec. 1, 2006, 8 pgs.

(Continued)

*Primary Examiner* — Ruth S Smith
*Assistant Examiner* — Christopher Cook
(74) *Attorney, Agent, or Firm* — Brooks, Cameron & Huebsch, PLLC

(57) ABSTRACT

Methods, apparatus, and systems for repairing defective occlusions are provided. One embodiment includes an elongate body having a first lumen extending from a proximal end toward a distal end of the elongate body. An elongate structure, having a lumen extending from a proximal end toward a distal end of the elongate structure, is extendably and rotatably positioned at least partially within the first lumen of the elongate body. An energy emitting device is coupled to a portion of the elongate body proximal the distal end of the elongate body to emit focused ultrasound.

16 Claims, 14 Drawing Sheets

U.S. PATENT DOCUMENTS

| | | |
|---|---|---|
| 2002/0173688 A1 | 11/2002 | Chen et al. |
| 2002/0183787 A1 | 12/2002 | Wahr et al. |
| 2003/0013971 A1 | 1/2003 | Makin et al. |
| 2003/0045901 A1 | 3/2003 | Opolski |
| 2003/0050665 A1 | 3/2003 | Ginn |
| 2003/0144694 A1 | 7/2003 | Chanduszko et al. |
| 2003/0181945 A1 | 9/2003 | Opolski et al. |
| 2003/0191495 A1 | 10/2003 | Ryan et al. |
| 2003/0208232 A1 | 11/2003 | Blaeser et al. |
| 2003/0216759 A1 | 11/2003 | Burbank et al. |
| 2003/0225421 A1 | 12/2003 | Peavey et al. |
| 2004/0073242 A1 | 4/2004 | Chanduszko |
| 2004/0087968 A1 | 5/2004 | Core |
| 2004/0092973 A1 | 5/2004 | Chanduszko |
| 2004/0093017 A1 | 5/2004 | Chanduszko |
| 2004/0098121 A1 | 5/2004 | Opolski |
| 2004/0127855 A1 | 7/2004 | Core |
| 2004/0127917 A1 | 7/2004 | Ginn |
| 2004/0133236 A1 | 7/2004 | Chanduszko |
| 2004/0158264 A1 | 8/2004 | Adams et al. |
| 2004/0176788 A1 | 9/2004 | Opolski |
| 2004/0176797 A1 | 9/2004 | Opolski |
| 2004/0176799 A1 | 9/2004 | Chanduszko et al. |
| 2004/0193147 A1 | 9/2004 | Malecki et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0021016 A1 | 1/2005 | Malecki et al. |
| 2005/0034735 A1 | 2/2005 | Deem et al. |
| 2005/0043759 A1 | 2/2005 | Chanduszko |
| 2005/0059983 A1 | 3/2005 | Opolski et al. |
| 2005/0059984 A1 | 3/2005 | Chanduszko et al. |
| 2005/0070923 A1 | 3/2005 | McIntosh |
| 2005/0070952 A1 | 3/2005 | Devellian |
| 2005/0080406 A1 | 4/2005 | Malecki et al. |
| 2005/0080430 A1 | 4/2005 | Wright, Jr. et al. |
| 2005/0085843 A1 | 4/2005 | Opolski et al. |
| 2005/0101984 A1 | 5/2005 | Chanduszko et al. |
| 2005/0119524 A1 | 6/2005 | Sekine et al. |
| 2005/0131401 A1 | 6/2005 | Malecki et al. |
| 2005/0131460 A1 | 6/2005 | Gifford, III et al. |
| 2005/0228283 A1* | 10/2005 | Gifford et al. ............ 600/459 |
| 2005/0251210 A1 | 11/2005 | Westra et al. |
| 2005/0267495 A1* | 12/2005 | Ginn et al. |
| 2007/0043318 A1 | 2/2007 | Sogard et al. |
| 2007/0043337 A1 | 2/2007 | McAuley |
| 2007/0060858 A1* | 3/2007 | Sogard et al. |

FOREIGN PATENT DOCUMENTS

| | | |
|---|---|---|
| WO | 0217809 | 3/2002 |
| WO | 2005027753 | 3/2005 |
| WO | 2005039419 | 5/2005 |

OTHER PUBLICATIONS

European Office Action in related European Patent Application No. 06 80 1341.6. Jan. 13, 2011. 6 pgs.

\* cited by examiner

OCCLUSION DEVICE

FIELD OF THE INVENTION

The present disclosure relates generally to apparatus, systems, and methods for use in the human body, more particularly to apparatus, systems, and methods to close a defective occlusion in the heart.

BACKGROUND

The human heart is divided into four chambers. These include the right atrium, the right ventricle, the left atrium, and the left ventricle. The right atrium and right ventricle are divided from the left atrium and left ventricle by a muscular wall call the septum. The atrial septum is the wall separating the atria and the ventricular septum is the wall separating the ventricles.

Early in fetal development the two atria (i.e., left and right atriums) are a single chamber. A wall or membranous structure develops from the inferior aspect of the atrial chamber and extends superiorly toward the base of the atrial chamber. This membrane is the septum primum (SP). As the SP seals to the base of the chamber, it is dissolved away at the superior attachment, creating a passageway for blood to travel from the right atria to the left atria (bypassing the developing lungs). At about the same time, a second membrane develops from the superior aspect of the right atrium and extends inferiorly. This membrane is the septum secundum (SS). It fuses with the SP along the walls of the atria, but does not extend to the base of the atria. The inferior portion of the SS is named the limbus. The two membranes form a passage defined by thin tissue (SP) and thick tissue (SS) that extends from the right atria to the left atria. This passage is named the foramen ovale. The portion of the SP that comprises the left side of the foramen ovale is named the fossa ovalis. The limbus of the SS is distinct from the fossa ovalis of the SP in that it is thicker and more muscular.

Upon birth blood must be diverted into the lungs of the newborn. One event that enables this is an increase in pressure within the left atrium relative to the right atrium. This pressure reversal effectively closes the foramen ovale and eliminates the shunting of blood from right to left. In most people, the SP and SS membranes that form the passage of the shunt fuse and the passage is eliminated. However, in a minority of people, these membranes do not fuse effectively and the shunt remains sealed by pressure, but the passage remains viable, or patent. This condition is named patent foramen ovale (PFO). In unusual circumstances the pressure in the right atrium can exceed that in the left atrium, allowing passage of blood through the PFO. This would typically be inconsequential, except when the venous (right atrial) blood contains thrombotic debris that is normally eliminated by thrombolytic mechanisms in the lungs. In this case, a clot can travel to the left atria and become an embolic risk to the patient's health through myocardial infarction or stroke. Other examples of occlusion defects can include patent ductus arteriosus (PDA), which is a tubular communication between the pulmonary artery and the aorta, and ventricular septal defects (VSDs). Although the causes and physical characteristics of these defects can vary, each of these defects is generally a small passage, flap, or hole in the septum which allows blood to shunt between chambers in the heart where there is generally no blood flow in a normal, healthy heart. Shunting of this type can also result in a number of health problems.

DETAILED DESCRIPTION

Figure 1:
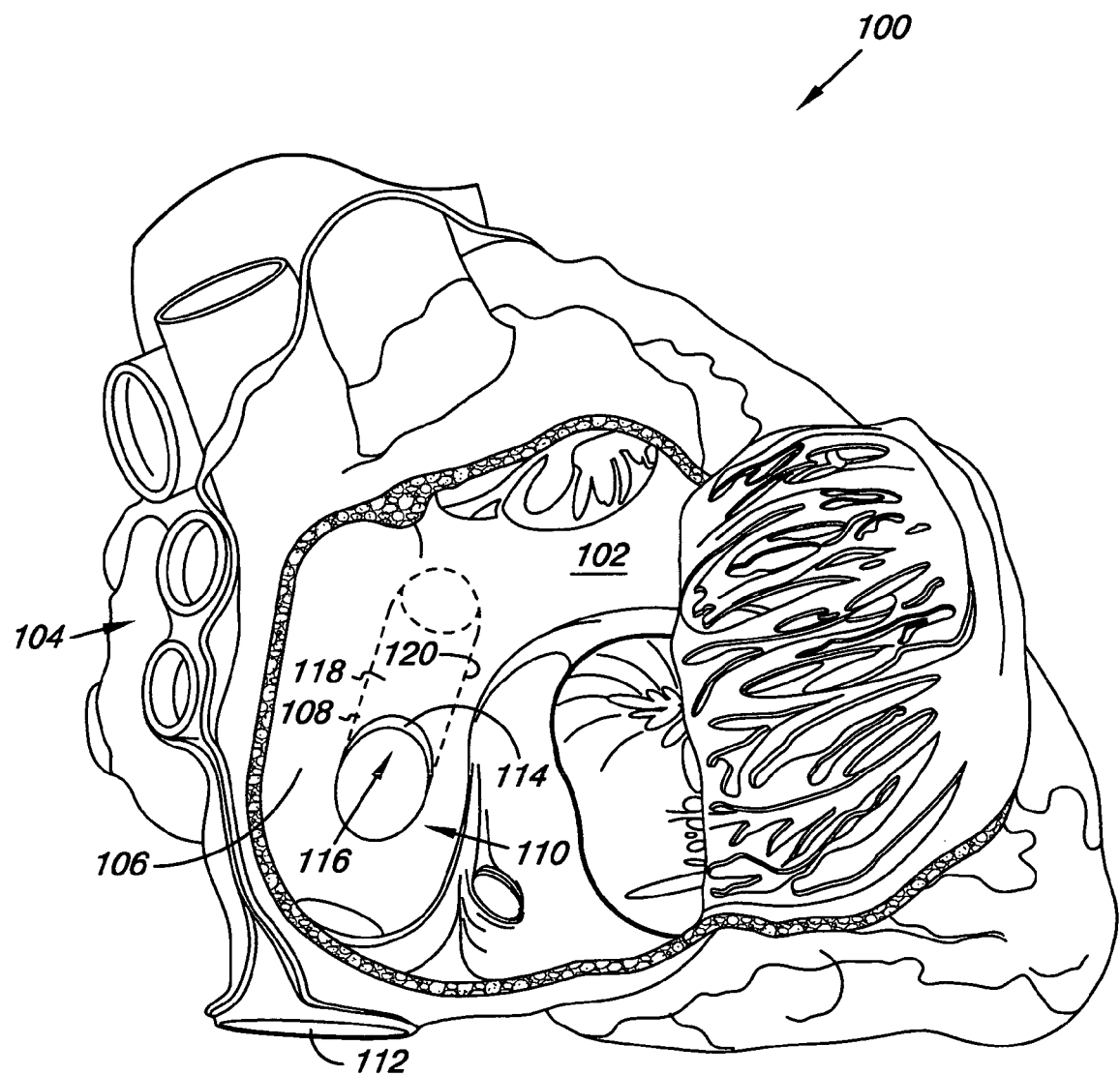
FIG. 1 illustrates a cross-sectional view of the heart.

Embodiments of the present disclosure are directed to methods, apparatus, and systems for closing defective occlusions, such as vascular or septal defects. The embodiments described herein are illustrated with reference to occluding a patent foramen ovale (PFO), which is an opening in the atrial septum defined by tissues of the septum secundum and septum primum. For example, in various embodiments, occluding a PFO can be accomplished through the use of an occlusion device delivered to the right atrium by a delivery catheter. In various embodiments, the occlusion device can be positioned such that a portion of the occlusion device sits on the limbus of the septum secundum. Seating the occlusion device on the limbus helps to locate an elongate structure at a position on the atrial septum where two membranes, the SS and the septum primum (SP), lie parallel to one another. This position makes possible the use of the various embodiments described herein to seal a PFO, (e.g., seal the passage defined by the SS and SP). As used herein, septum secundum can be referred to as thick tissue and septum primum can be referred to as thin tissue. As used herein, a patent foramen ovale is a passage defined by the thick and thin tissue.

In various embodiments, once the elongate structure is properly positioned, a tissue apposition member can be extended from the elongate structure and advanced through the thick tissue and thin tissue of the passage. The tissue apposition member can include an extendable apposition arm which can be used to bring the tissues of the passage together so as to temporarily occlude the PFO. In such embodiments, an energy emitting device can apply ultrasound focused to a high intensity to the tissues so as to fuse the tissues together and occlude the PFO.

Thus, in various embodiments, by manipulating various components of the occlusion device (e.g., tissue apposition members, elongate structure and/or energy emitting device) the tissues of the passage can be brought together and the PFO can be occluded.

In various embodiments, a system can include at least one ultrasound energy emitting device configured to emit a focused ultrasound beam at varying levels of intensity. The system can include a targeting device configured to provide a target for the focused ultrasound and a catheter that includes an occlusion device extendably positioned between a proximal end and a distal end of the catheter. In such a system, focused ultrasound can be delivered to a target provided by the targeting device from within the human body and from outside the human body.

As will be discussed herein, in the various embodiments of the present disclosure, tissues can be brought together before, during, and/or after applying energy to the tissues. The use of focused ultrasound and other types of energy (e.g., RF energy) on tissues denatures the collagen in the tissues. Tissue that undergo denaturization will tend to renature. If tissues brought together remain in contact while they renature, the collagen in the tissues brought together will effectively combine to fuse the once separated tissues together.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the occlusion device according to the present disclosure.

The method, apparatus, and system embodiments described herein are illustrated with reference to occluding a patent foramen ovale (PFO). However, the method, apparatus, and system embodiments can also be used to occlude other defective occlusions. For example, using the various method, apparatus, and system embodiments described herein, other defective occlusions such as patent ductus arteriosus, atrial septal defects (ASDs), and ventricular septal defects (VSDs) can be occluded.

In FIG. 1, a right lateral view of the heart 100 is shown with an opened right atrium 102. The heart 100 is divided into four chambers, which are referred to herein as the right atrium 102, a right ventricle, a left atrium 104 and a left ventricle. Heart 100 also includes a septal wall 106 that divides the four chambers of the heart. The portion of the septal wall dividing the left and right atriums 102 and 104 is called the interatrial septum 108. The portion of the septal wall 106 dividing the left and right ventricle is called the ventricular septum.

The fossa ovalis 110 is situated at the lower part of the atrial septum 108, above and to the left of the orifice of the inferior vena cava 112. The limbus 114 of the septum secundum 118 is the pronounced anterosuperior margin of the fossa ovalis 110 within the right side (i.e., the right atrium 102) of the interatrial septum 108. It represents the inferior margin of the septum secundum during fetal life.

The passage 116 can be defined by surfaces of the SS (thick tissue) and surfaces of the SP (thin tissue) and extends between the right and left atriums 102 and 104. The thick tissue 118 forms the right margin of the passage 116 and comprises the superior portion of the interatrial septum 108. Thus, the thick tissue 118 is located adjacent the limbus 114 and extends upward and rightward away from the limbus 114. The thin tissue 120 forms the left margin of the passage 116 and comprises the inferior portion of the interatrial septum 108 (i.e., below the thick tissue 118) and extends upward and rightward substantially parallel to the thick tissue 118 and toward the left atrium 104.

Figure 2A:
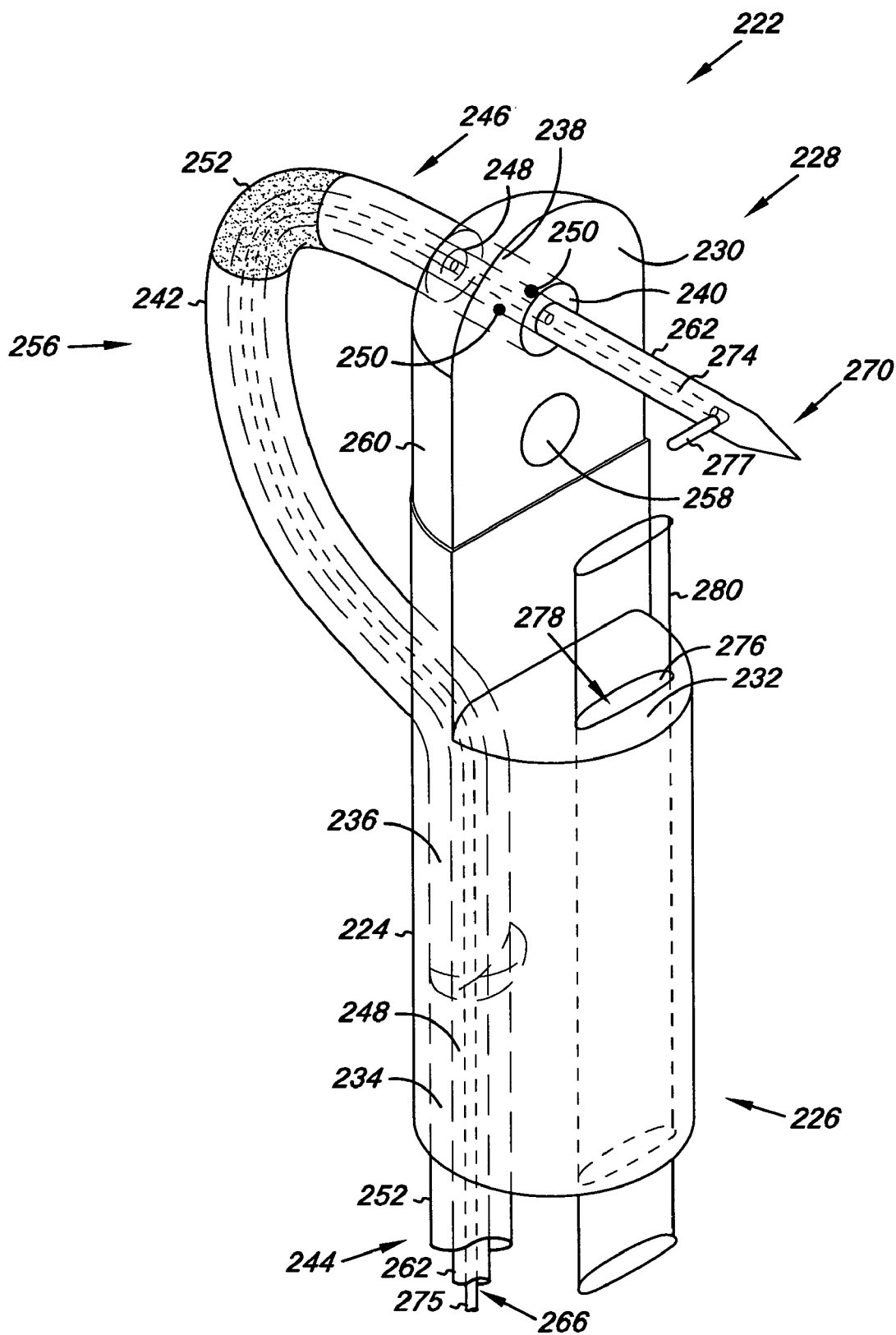
FIG. 2A illustrates an embodiment of an occlusion device according to the teachings of the present disclosure.

FIG. 2A provides an illustration of an occlusion device 222 that can be used to bring the thick and the thin tissues of the passage together and to fuse them by the application of energy. In various embodiments in FIG. 2A, occlusion device 222 includes an elongate body 224 having a proximal end 226 and a distal end 228. The elongate body 224 further includes a wall 230 that extends from the distal end 228 toward the proximal end 226. In the embodiment shown in FIG. 2A, the wall 230 includes a planar surface. However, in various embodiments, the wall 230 can include other types of surfaces. For example, in some embodiments, the wall 230 can include non-planar surfaces such as a convex surface or a concave surface.

The wall 230 extends toward the proximal end 226 to a ledge 232 that extends away from the wall 230. In various embodiments, the ledge 232 extends perpendicularly away from the wall 230 for a predetermined distance. The ledge 232 includes a planar surface whose outer edge defines a semicircular shape. As will be discussed herein, the ledge 232 of the occlusion device 222 allows the occlusion device 222 to be seated on the limbus of the septum secundum of a patient's heart.

The elongate body 224 of the occlusion device 222 can be constructed from a number of materials. Examples of materials include, but are not limited to, metal, metal alloys, and polymeric materials, natural and synthetic materials.

Since the size and shape of the limbus can vary from patient to patient, the occlusion device 222, including the wall 230 and the ledge 232 can include various shapes and sizes that can be based on the anatomical structures of a patient's heart including the limbus of the septum secundum. For example, in some embodiments, the ledge 232 can have a surface defining various geometric shapes and sizes, including, but not limited to, convex shapes, concave shapes, recessed shapes, and irregular shapes, among others. In addition, in some embodiments, the ledge 232 can extend at various angles other than perpendicular from the wall 230 of the elongate body 224.

The occlusion device 222 includes a number of lumens that extend various lengths within the occlusion device 222. In various embodiments, the occlusion device 222 includes a first lumen 234. In various embodiments, the first lumen 234 can extend toward the distal end 228 of the elongate body 224. In the embodiment illustrated in FIG. 2A, the first lumen 234 extends toward the distal end 228 of the elongate body 224 to communicate with a channel 236.

The channel 236 is defined by the surface of the elongate body 224 and extends longitudinally between the first lumen 234 and a second lumen 238.

The second lumen 238 extends from a first opening 240, which is defined by the surface of the wall 230. The second lumen 238 extends from the first opening 240 and through the elongate body 224. In various embodiments, the second lumen 238 extends through the elongate body to communicate with the channel 236, as discussed herein. In various embodiments, the second lumen 238 is perpendicular relative to the first lumen 234 and the channel 236. However, in some embodiments, the second lumen 238 can be angled other than perpendicularly relative to the first lumen 234 and the channel 236.

In various embodiments described herein, the first lumen 234, the channel 236, and the second lumen 238 can form a contiguous conduit in which components of the occlusion device 222 can be positioned, extended, and/or retracted. For example, one such component can include a elongate structure 242. In various embodiments in FIG. 2A, the elongate structure 242 includes a proximal end 244 and a distal end 246. The elongate structure 242 also includes a lumen 248 that extends longitudinally between the proximal end 244 and the distal end 246 of the elongate structure 242. In various embodiments, the elongate structure 242 can be extendably positioned within the first lumen 234 of the elongate body 224 toward the distal end 228 of the elongate body 224. In such embodiments, as the elongate structure 242 extends toward the distal end 228 of the elongate body 224, it passes through the first lumen 234, the channel 236, and to the second lumen 238.

In various embodiments, the elongate structure 242 can include a rotation point 250 along which the distal end 246 of the elongate structure 242 can rotate. In various embodiments in FIG. 2A, the rotation point 250 includes two pivots coupled to an outer surface of the elongate structure 242. In turn, the pivots can be rotatably coupled to surfaces defining the channel 236 or the second lumen 238 proximal the distal end 228 of the elongate body 224. In an alternative embodiment, the rotation point 250 can be defined by surfaces of the second lumen 238. In the alternative embodiment, the surfaces of the second lumen 238 can be formed to provide the rotation point 250 along which the distal end 246 of the elongate structure 242 can rotate. In such an embodiment, the elongate structure 242 would not require pivots.

The elongate structure 242 can include a flexible portion 252. The flexible portion 252 can be configured as a region of the elongate structure 242 that is more flexible as compared to other portions of the elongate structure 242. For example, in some embodiments, the flexible portion 252 of the elongate structure 242 can be formed of a flexible plastic and/or metal that can bend without obstructing the lumen 248 of the elongate structure 242. A portion of the elongate structure 242 extending from the flexible portion 252 toward the proximal end 244 of the elongate structure 242 can be formed of a semi-flexible plastic and/or metal that can bend, but not as easily as the flexible portion 252. And, a portion of the elongate structure 242 extending from the flexible portion 252 toward the distal end 246 of the elongate structure 242 can be formed of a substantially rigid plastic and/or metal so as not to bend.

In the embodiments described herein, the rotation of the elongate structure 242 is accompanied by a predetermined bend of the elongate structure 242. That is, the rotation occurs along the rotation point 250 and the predetermined bend occurs along the flexible portion 252 of the elongate structure 242.

Figure 2B:
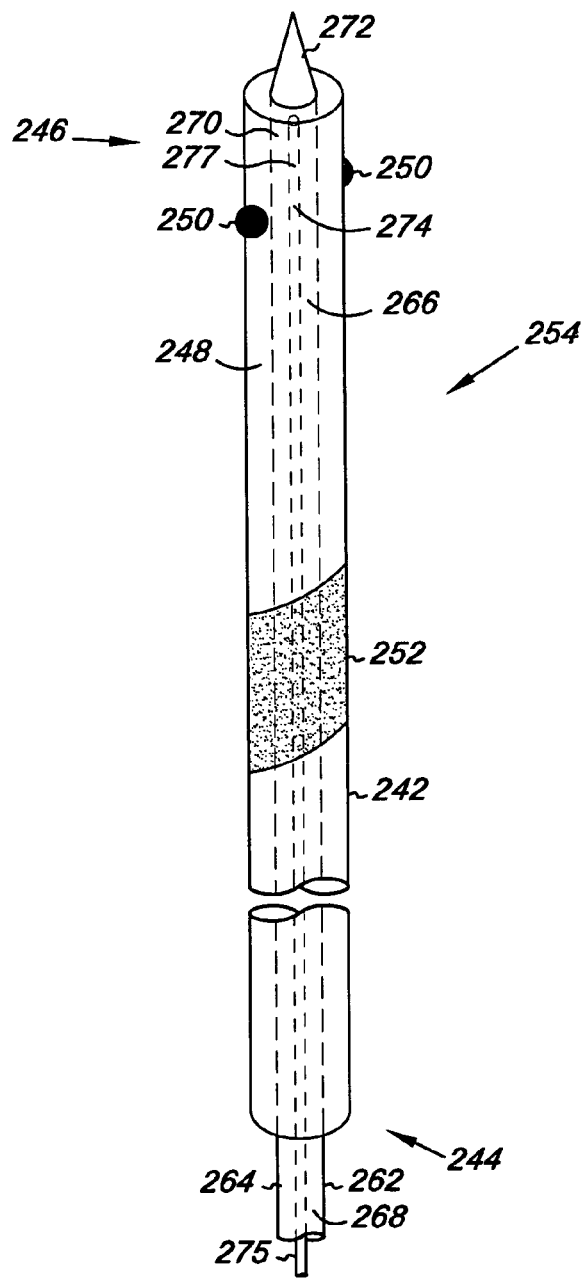
FIG. 2B shows an embodiment of a elongate structure in a first position.

FIG. 2B illustrates an embodiment of the elongate structure 242 illustrated in FIG. 2A. For ease of illustration, in FIG. 2B, the elongate structure 242 is illustrated in a first position 254, without the occlusion device 222. By contrast, in FIG. 2A, the elongate structure 242 is extended away from the channel 236 (i.e., a second position 256). In the first position 254, the elongate structure 242 can be extendably positioned within the first lumen 234, the channel 236, and the second lumen 238 of the elongate body 224, described in connection with FIG. 2A. As mentioned above, in the second position 256, a portion of the elongate structure 242 proximal to and at the distal end 246 is rotated substantially 90 degrees relative to the elongate body 224 of the occlusion device 222. Rotating the elongate structure substantially 90 degrees can position a tissue apposition member 262 extendably positioned within a lumen of the elongate structure 242 substantially perpendicular to the thick tissue (i.e., septum secundum). However, in various embodiments, the elongate structure 242 can be rotated more than 90 degrees and less than 90 degrees.

Movement from the first position 254 to the second position 256 can result from a compression force applied to the elongate structure 242. As used herein, the compression force is a force applied through the elongate structure 242 to impart compression on the rotation point 250 of the elongate structure 242. The compression force can originate from the proximal end 244 of the elongate structure 242 by pushing the proximal end 244 of the elongate structure 242.

In various embodiments, a deployment rod, as will be discussed herein, can be used to push the proximal end 244 of the elongate structure 242. In various embodiments, an operator can grasp the proximal end 244 of the elongate structure 242 and push it without using a deployment rod.

As mentioned above, the compression force acts on the pivots of the rotation point 250. As the compression force increases, a column strength of the elongate structure is eventually overcome such that the flexible portion 252 of the elongate structure 242 begins to bend relative to the remainder of the elongate structure 242. As the flexible portion 252 begins to bend, the elongate structure 242 begins to extend away from the channel 236 of the elongate body 224. As the elongate structure 242 extends away, the predetermined bend of the flexible portion 252 begins to form as the distal end 246 of the elongate structure 242 rotates along the rotation point 250 to the second position 256.

At the second position 256, the distal end 246 of the elongate structure 242 is positioned substantially 90 degrees relative to the elongate body 224 and is temporarily secured in the second position 256. Securing the elongate structure 242 in the second position 256 can include a number of methods. In various embodiments, for example, a deployment rod, used to apply the compression force can, can also be used to secure the elongate structure in the second position.

To move from the second position 256 to the first position 254, a pulling force can be applied to the proximal end 244 of the elongate structure 242 to pull the elongate structure 242 from the second position 256 to the first position 254. For example, in some embodiments, the pulling force can be the result of pulling the proximal end 244 of the elongate structure 242 using a deployment rod. likewise, an operator can grasp the proximal end 244 of the elongate structure 242 and apply the pulling force without using a deployment rod.

In various embodiments, the elongate body 224 of the occlusion device 222 can include an extendable portion 260, as shown in FIG. 2A. In such embodiments, the extendable portion 260 can be located proximal to the distal end 228 of the elongate body 224. The extendable portion 260 functions to increase a length of the elongate body 224. For example, in various embodiments, the extendable portion 260 can be extended by applying a compression force at the proximal end 244 of the elongate structure 242. As discussed herein, the compression force applied to the elongate structure 242 pushes the elongate structure 242 away from the channel 236 of the elongate body 224 to move the elongate structure 242 to the second position 256. At the second position 256, if the compression force continues to be applied to the elongate structure 242, surfaces at the distal end 246 of the elongate structure 242 transfer the compression force to surfaces of the second lumen 238, which in turn, allow the extendable portion 260 of the elongate body 224 to move upward, similar to telescoping an antenna. As will be discussed herein, extending the extendable portion 260 of the elongate body 224 upward results in changing a location of both a tissue apposition member and an energy emitting device 258 that can be coupled to the occlusion device 222 so as to vary a location along tissues of the passage in which the tissue apposition member brings the tissues together. Extending the extendable portion can also vary the location along tissues of the passage in which energy is applied by the energy emitting device 258. Varying these locations allows an operator of the occlusion device to fuse tissues of the passage at varying locations, as will be discussed with respect to FIGS. 4A-5E.

The energy emitting device 258 is a device that can emit various types of energy including, but not limited to, high intensity ultrasound, low intensity ultrasound, RF energy, cryogenic energy, laser, resistive heat energy, and microwave. Energy emitting devices may have a number of different configurations, which can depend on the type of device, its placement location relative to the occlusion device on or physically separate from the occlusion devices, as well as its operational methods as intended. For example, in some embodiments, the energy emitting device 258 can include a high intensity focused ultrasound (HIFU) transducer coupled to the occlusion device 222. In various embodiments, the energy emitting device 258 can be coupled to the occlusion device 222 and positioned proximal the distal end 228 of the occlusion device 222, as shown in FIG. 2A. In such embodiments, one of ordinary skill in the art will understand that conductors can be coupled to the energy emitting device 258 to provide power to the energy emitting device 258. In addition, other components can be operatively coupled to the occlusion device 222, including, but not limited to, a signal generator, amplifier, computer, and targeting device, as will be discussed in connection with FIGS. 3A-3B.

In other embodiments, the energy emitting device 258 can be physically separated from the occlusion device 222. For example, in various embodiments, the energy emitting device 258 can be positioned within a human body but separate from the occlusion device 222 (e.g., proximal to and/or distal to the occlusion device 222). In some embodiments, the energy emitting device can be positioned outside the human body, as will be discussed with respect to FIGS. 3A and 3B. In such embodiments, the energy emitting device can be a HIFU transducer configured to emit focused ultrasound at a high intensity through tissues of the human body to a target within the human body, as will be discussed herein.

Figure 2C:
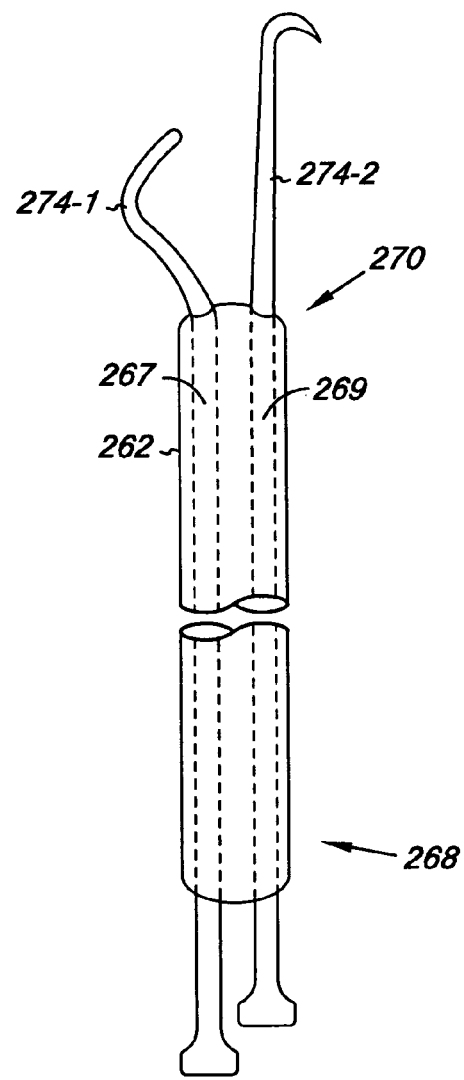
FIG. 2C illustrates an embodiment of a tissue apposition member according to the teachings of the present disclosure.

In FIGS. 2B and 2C, various embodiments of a tissue apposition member 262 are illustrated. In the embodiments described in FIGS. 2B and 2C, the tissue apposition member 262 functions to bring tissues of the passage together (i.e., septum secundum and septum primum) prior to fusing them with the energy emitting device. To do this, various embodiments of the tissue apposition member 262 can include a variety of configurations and can be positioned in a variety of locations. For example, in some embodiments, the tissue apposition member 262 can be extendably positioned within the lumen 248 of the elongate structure 242, as shown in FIG. 2B. In other embodiments, the tissue apposition member 262 can be extendably positioned within a lumen of a catheter, as will be discussed in more detail herein. And, in various embodiments, the tissue apposition member 262 can be extendably positioned within a third lumen 276 of the occlusion device, as will also be discussed in more detail herein.

Referring now to the embodiment of the tissue apposition member in FIGS. 2A and 2B, the tissue apposition member 262 is extendably positioned within the lumen 248 of the elongate structure 242. As shown in the embodiment of FIG. 2B, the tissue apposition member 262 includes an elongate body 264 having a lumen 266 extending from a proximal end 268 toward a distal end 270 of the tissue apposition member 262. At the distal end 270, the tissue apposition member 262 includes a piercing structure 272. In various embodiments, the piercing structure 272 includes a pointed tip that allows the tissue apposition member 262 to pierce the tissue of the passage (i.e., septum secundum and septum primum). The tissue apposition member 262 can include at least one pulling member 274 extendably positioned within the lumen 266 of the tissue apposition member 262. The pulling member 274 can include a proximal and a distal end 275 and 277, as shown in FIGS. 2A and 2B. In various embodiments, the distal end 277 can be extended from the lumen 266 of the tissue apposition member 262 and through an opening at defined by a surface of the tissue apposition member 262 at the distal end 270 of the tissue apposition member 262, as shown in FIG. 2A. When the distal end 277 of the pulling member 274 is extended from the lumen 266 and through the opening of the tissue apposition member 262, it extends radially from the surface of the tissue apposition member 262. In various embodiments, the radially extending pulling member 274 can catch tissue of the passage and bring tissues together through manipulation of the tissue apposition member 262 and/or the pulling member 274.

Referring now to FIG. 2C, the tissue apposition member 262 includes a different configuration. In various embodiments of FIG. 2C, the tissue apposition member 262 includes two pulling members; a first pulling member 274-1 and a second pulling member 274-2 that can be used to manipulate tissue of the passage (i.e., septum secundum and septum primum). The pulling members 274-1 and 274-2 extend between the proximal and the distal end 268 and 270 of the tissue apposition member 262. In this embodiment, the tissue apposition member 262 includes a first and a second lumen 267 and 269 that extend between the proximal and the distal end 268 and 270 of the tissue apposition member 262. At the distal end 270, the tissue apposition member 262 includes surfaces that define two openings through which the. In various embodiments, the two pulling members 274-1 and 274-2 can be positioned within the first and second lumens 267 and 269 and extend from the tissue apposition member 262 via the two openings through which the two pulling members 274-1 and 274-2 can move.

In various embodiments, the pulling members 274-1 and 274-2 can include a variety of shapes and sizes that allow for the pulling members 274-1 and 274-2 to clamp, grasp, grip, hook, pierce, catch, vacuum, push, pull, and/or trap, e.g., tissues of the passage, to bring them together or otherwise manipulate them. In the embodiment illustrated in FIG. 2C, the pulling members 274-1 and 274-2 are illustrated as having one or more predefined shapes that help to position the pulling members adjacent the thick tissue (septum secundum) and thin tissue (septum primum) of the passage. For example, the shapes illustrated in FIG. 2C help to push, hook, and pull the thick and the thin tissue of the passage to bring them together.

Examples of suitable materials for forming the tissue apposition member including pulling members and other components of the tissue apposition member illustrated in FIGS. 2A-2C can include, but are not limited to, metals, metal alloys, and/or polymer materials. Specific examples of such materials can include shape memory metals such as Nitinol, linear-elastic Nitinol, super-elastic Nitinol, shape memory polymers, medical grade stainless steel (e.g., 316L), titanium, tantalum, platinum alloys, niobium alloys, cobalt alloys, alginate, MP35N, aluminum alloys, chromium alloys, copper alloys, vanadium alloys, or combinations thereof. Examples of plastics can include shape memory plastics, polymers, and thermoplastic materials. Other materials are also contemplated.

These materials can allow for forming and setting the predefined shape of the pulling members. These materials allow the pulling members to resiliently flex to be compressed when in their respective lumens, and then extend toward the predefined shape as they extend from their respective lumens.

Referring again to FIG. 2A, in various embodiments, the tissue apposition member 262 can be positioned at other locations of the occlusion 222. For example, in the embodiment illustrated in FIG. 2A, a tissue apposition member can be positioned within a third lumen 276 of the occlusion device 222.

In various embodiments of FIG. 2A, the third lumen 276 extends toward ledge 232 and communicates with a second opening 278 defined by the surface of the ledge 232. In various embodiments, the tissue apposition member 262 can include a suction arm 280 that can extend within the third lumen 276 of the elongate body 224 and away from the ledge 232 of the elongate body 224 through the second opening 278. In such embodiments, the suction arm 280 can be positioned within the passage and proximal to thick and thin tissue of the passage. In various embodiments, the suction arm 280 can be used for engaging the thick and thin tissues within the passage. For example, the suction arm 280 can apply a vacuum force to the tissues to bring them together or otherwise maneuver their position, as will be discussed herein.

Figure 3A:
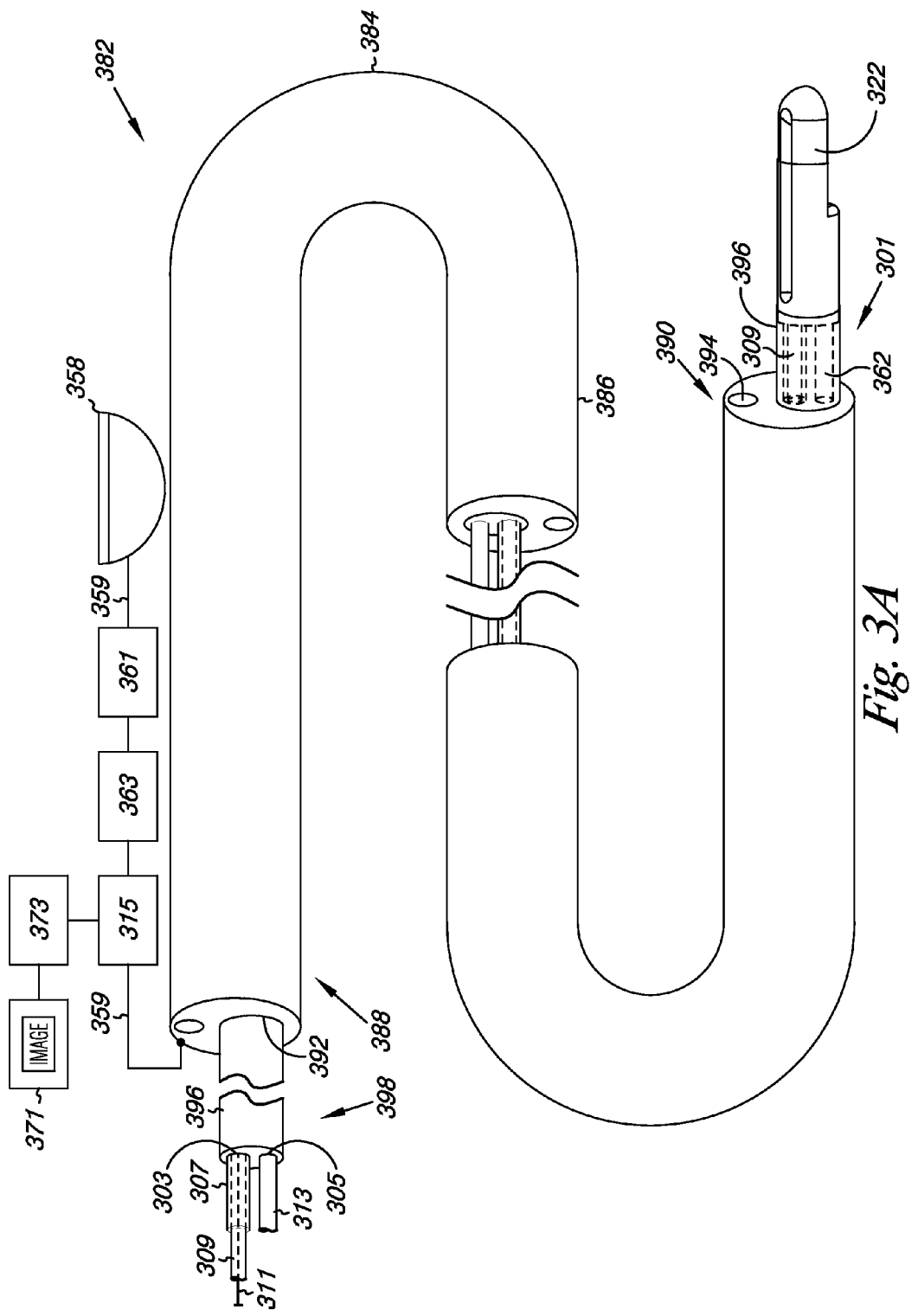
FIG. 3A illustrates an embodiment of a system of the present disclosure.
Figure 3B:
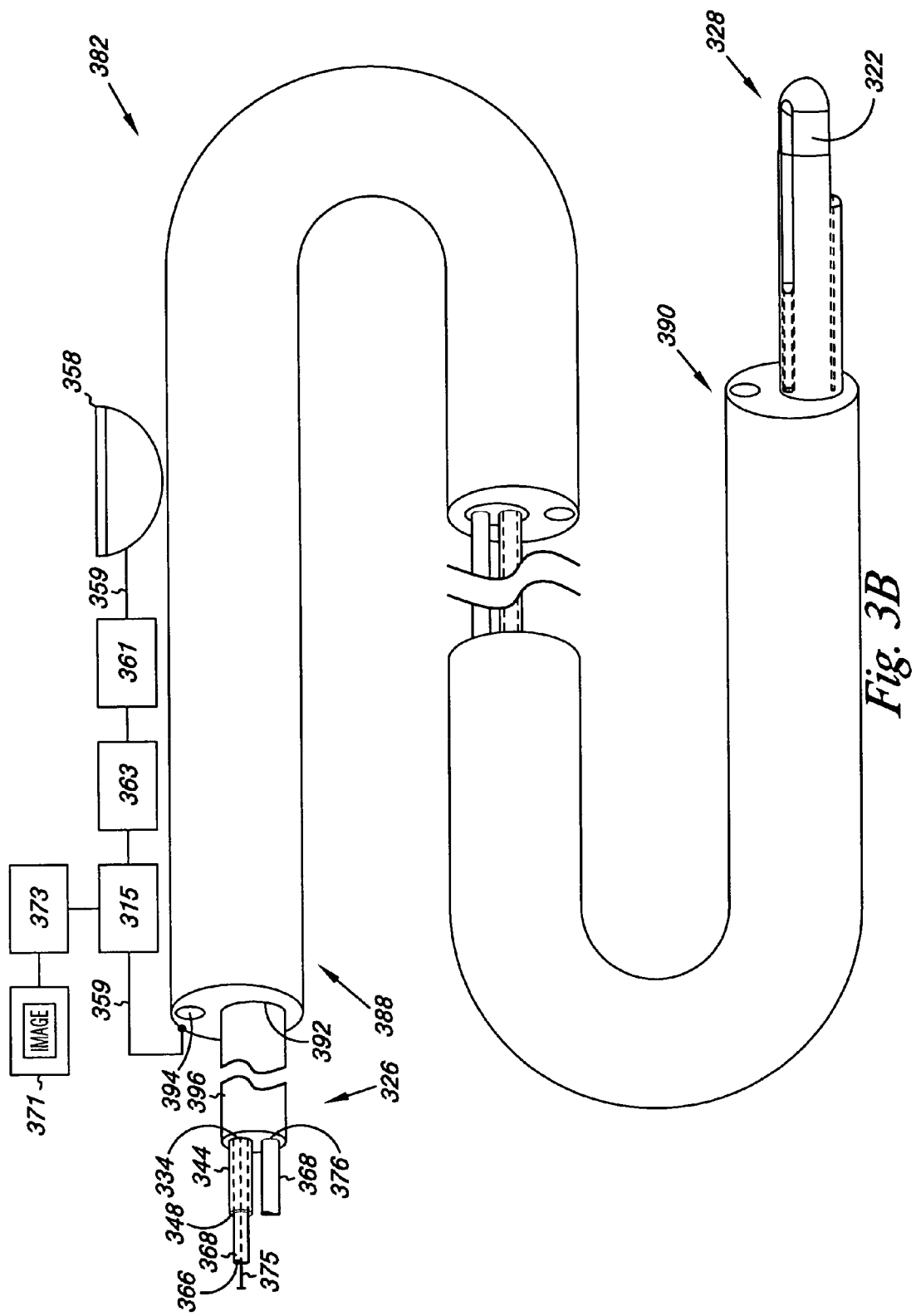
FIG. 3B illustrates another embodiment of a system of the present disclosure.

FIGS. 3A-3B illustrate various embodiments of a system 382 that includes the occlusion device 322, as the same is described herein. In various embodiments, system 382 includes a catheter 384. The catheter 384 includes an elongate body 386 having a proximal end 388 and a distal end 390. The catheter 384 includes lumen 392 such that the occlusion device 322 can travel within the catheter 384 along the length of the catheter 384.

The catheter 384 can further include a guidewire lumen 394. The guidewire lumen 394 can extend within and along the length of the elongate body 386 of the catheter 384 from the proximal end 388 to the distal end 390 of the catheter 384. In various embodiments, the guidewire lumen 394 can receive a guidewire for positioning the catheter 384 and the occlusion device 322 within a heart chamber e.g., a right atrium of a patient. In various embodiments, the guide wire lumen 394 and the lumen 392 can include various configurations. For example, in some embodiments, the guidewire lumen 394 and the lumen 392 can include a dual lumen configuration within the catheter 384, as shown in FIG. 3A. In other embodiments, the guidewire lumen 394 and the lumen 392 can include a coaxial configuration within the catheter 384.

In various embodiments, the system 382 can include a sheath 396. The sheath includes a proximal end 398 and a distal end 301. In some embodiments, the sheath 396 can be slidably positioned within the lumen 392 of the catheter 384. In various embodiments, the occlusion device 322 is coupled to the sheath 396 at the distal end 301 of the sheath 396. The sheath 396, including the occlusion device 322 coupled thereon, can be slidably positioned within the lumen 392 of the catheter 384 to deploy the occlusion device 322 from the catheter 384.

The sheath 396 can include a number of lumens extending between the proximal end 398 and the distal end 301. As shown in the embodiment of FIG. 3A, the sheath 396 includes a first lumen 303 and a second lumen 305. In various embodiments, the first and second lumens 303 and 305 of the sheath 396 can accommodate the movement of deployment rods and other components of the system 382. Deployment rods can be used to deploy the various components e.g., the elongate structure 242 shown in FIGS. 2A and 2B, from the occlusion device 322 and/or catheter 384. In various embodiments, the first lumen 303 of the sheath 396 includes a first deployment rod 307 therein. In various embodiments, the first deployment rod 307 moves within the first lumen 303 of the sheath 396 and the first lumen of the elongate body 324 to extend the elongate structure 242 away from the channel 236 of the elongate body 224, as described in connection with FIGS. 2A-2B. The first deployment rod 307 can also be used to extend the extendable portion 260 of the occlusion device, as described in connection with FIG. 2A.

The system can include a second deployment rod 309. The second deployment rod 309 can be positioned adjacent the tissue apposition member positioned within the lumen of the elongate structure 242, as described in connection with FIGS. 2A-2C. In such an embodiment, the second deployment rod 309 moves within the lumen 248 of the elongate structure 242 to extend the tissue apposition member 262 from the lumen of the elongate structure, as described in connection with FIGS. 2A-2B.

The system can also include a third deployment rod 311. The third deployment rod 311 can be positioned adjacent the pulling member 274 positioned within the tissue apposition member 262 of the elongate structure 242 and moves within the lumen of the tissue apposition member 262 to extend the pulling member 274 as described in connection with FIGS. 2A-2B.

In various embodiments, the second lumen 305 can include a fourth deployment rod 313 positioned therein. In various embodiments, the fourth deployment rod 313 can be positioned adjacent the proximal end of the tissue apposition member 262 (suction arm 280) positioned within the third lumen 276 of the occlusion device 222 as described in connection with FIG. 2A. In such embodiments, the fourth deployment rod 313 moves within the second lumen 305 to extend the tissue apposition member 280 from the third lumen 276 of the occlusion device 222 via the second opening 278 of the occlusion device 322, as discussed in connection with FIG. 2A.

FIG. 3B illustrates another embodiment of system 382. In the embodiment illustrated in FIG. 3B, the occlusion device 322 is slidably positioned within the lumen 392 of the catheter 384 without the sheath. As the reader will appreciate, the distal end 328 of the occlusion device 322 is slidably positioned within the lumen 392 of the catheter 384 prior to delivery to a site within a human body and can be deployed from the distal end 390 of the catheter 384 by applying a pushing force to the proximal end 326 of the occlusion device 322. In addition, the various components of the occlusion device can be operated by directly grasping their proximal ends and manipulating them. For example, the proximal end 344 of the elongate structure from the first lumen 334 of the occlusion device 322. The proximal end 368 of the tissue apposition member can extend from the lumen 348 elongate structure, and the proximal end 375 of the pulling member can extend from the lumen 266 of the tissue apposition member. As one of ordinary skill will appreciate, such a configuration includes a coaxial lumen configuration. In addition, the proximal end of 368 of the suction arm can extend from the third lumen 376, as shown in FIG. 3B.

In various embodiments of the system 382, system 382 can include an energy emitting device, as described in connection with FIGS. 2A-2C. In various embodiments, the energy emitting device 358 can be a high intensity focused ultrasound (HIFU) transducer configured to emit focused ultrasound at a high intensity to a target, which can be provided by a targeting device 315. In some embodiments, the energy emitting device 358 is configured to emit HIFU to the target from outside the human body. In other embodiments, the energy emitting device 358 is configured to emit the focused ultrasound beam to the target from within the human body. In various embodiments, the energy emitting device 358 is operatively coupled to conductors 359, a signal generator 361, amplifier 363, a computer 373 including computer executable instructions (e.g., software), a display 371, and a targeting device 315, etc., as shown in the embodiments of FIGS. 3A and 3B.

As used herein, the targeting device 315 is a device that can provide a target and/or create a target and/or locate a target and/or help to guide, direct, etc., energy emitted from the energy emitting device 358 to the target. As used herein, a target is a location to which an energy emitting device 358 delivers energy, for example, tissues of a PFO. As used herein, providing and/or creating a target means visually defining a target using a display screen, e.g., 371, to display an image of tissue in which an operator can guide HIFU and/or using program instructions executing on a computer 373 to define a target using trigonometric algorithms (e.g., triangulation), dynamic depth focusing algorithms, etc., to which the HIFU is directed. As used herein, locating a target can include visually observing an image of the target (.e.g., an image of tissue) to which HIFU is to be directed.

In various embodiments, guiding, directing, etc., the HIFU to the target can include utilizing the targeting device 315 in conjunction with program instructions executing on a computer 373 coupled to the targeting device 315 and energy emitting device 358 to help guide the HIFU to the target. In various embodiments, guiding the HIFU to the target can include a manual process where the physician controls the direction of the HIFU, and other parameters such as frequency, intensity, and focus of the HIFU. In some embodiments, guiding the HIFU to the target can include an automated process where mechanical devices, such as robotic devices, controls the direction of the HIFU including the frequency, intensity, and focus, among other parameters involved in operating the targeting device 315 and the HIFU transducer 358. Other devices or systems that can be implemented to provide, create, and/or locate a target in which HIFU is guided can include Virtual Reality (VR) systems, and Augmented Reality Systems, where real-time information, such as an image of the PFO from the patient is integrated with that from a 3-D model of the patient's PFO from a Virtual Reality system.

In various embodiments, the targeting device 315 can include a single component or multiple components. In addition, the components of the targeting device can be located at a target, proximal to a target, and/or distal to the target. For example, in some embodiments, the targeting device can include multiple components where one component is located adjacent the target, and another component is located distal to the target. Examples of components of the targeting device can include, but are not limited to, imaging probes and devices (e.g., magnetic resonance imaging, ultrasound imaging, and optical imaging, etc.), Doppler devices (e.g., Doppler audio), software, computers, dynamic depth focusing devices, and targeting markers (e.g., ultrasound targeting icons, radiopaque markers, and the like). In various embodiments, the targeting device can include components that work in conjunction with one another to achieve better targeting, such as better imaging of the target. For example, an optical device and electromagnetic devices can be operatively and communicatively coupled such that the optical device can be used to recalibrate a magnetically based device in real time so that a magnetic tracker can take over from the optical device when sight-lines are broken.

In various embodiments, the targeting device 315 can include other functions such as monitoring the tissue for physical changes, visual changes, thermal changes, and the like. For example, in various embodiments, an operator of the targeting device 315 can monitor the temperature of the tissues of the passage after energy has been applied to determine if the tissues have sufficiently cooled and whether they have fused together. For example, in various embodiments, the targeting device can include a monitoring function that provides thermometric imaging that can provide a temperature map of the targeted area, as the same will be known and understood.

Multiple components can be employed in conjunction with the targeting device. For example, catheter 384 can include temperature sensors coupled to the distal end 390 of the catheter 384. In other embodiments, the occlusion device 322 can include temperature sensors coupled to the occlusion device and/or various components of the occlusion device (e.g., tissue apposition member). Embodiments are not limited to these examples.

In various embodiments, the targeting device can be located outside the human body. In various embodiments, the targeting device can include an imaging ultrasound device for providing images of the target from outside the human body. In another embodiment, the targeting device can include a magnetic resonance imaging device for providing images of the target from outside the human body. In some embodiments, the targeting device can include X-rays for providing images of the target using radiopaque markers positioned at or adjacent to the target. In various embodiments, the targeting device can include a Doppler imaging system to help guide high intensity focused ultrasound to the target by visual or audio guidance.

The various embodiments of the targeting device can be configured to provide real-time images of the target (e.g., a real time imaging ultrasound device, a real time MR imaging device, a real time optical imaging device, etc.). The real-time images can be provided before, during, and/or after the application of energy to the target. For example, in various embodiments, a targeting device that includes an imaging ultrasound device can be configured to provide real-time images of the target such that an operator of the energy emitting device can apply energy to the target while simultaneously viewing the target. Such embodiments allow the operator to verify that energy emitted from the energy emitting device is correctly guided to the target. Such embodiments also provide the operator with real-time monitoring of changes to tissues induced by the application of energy to the tissues.

Figure 4A:
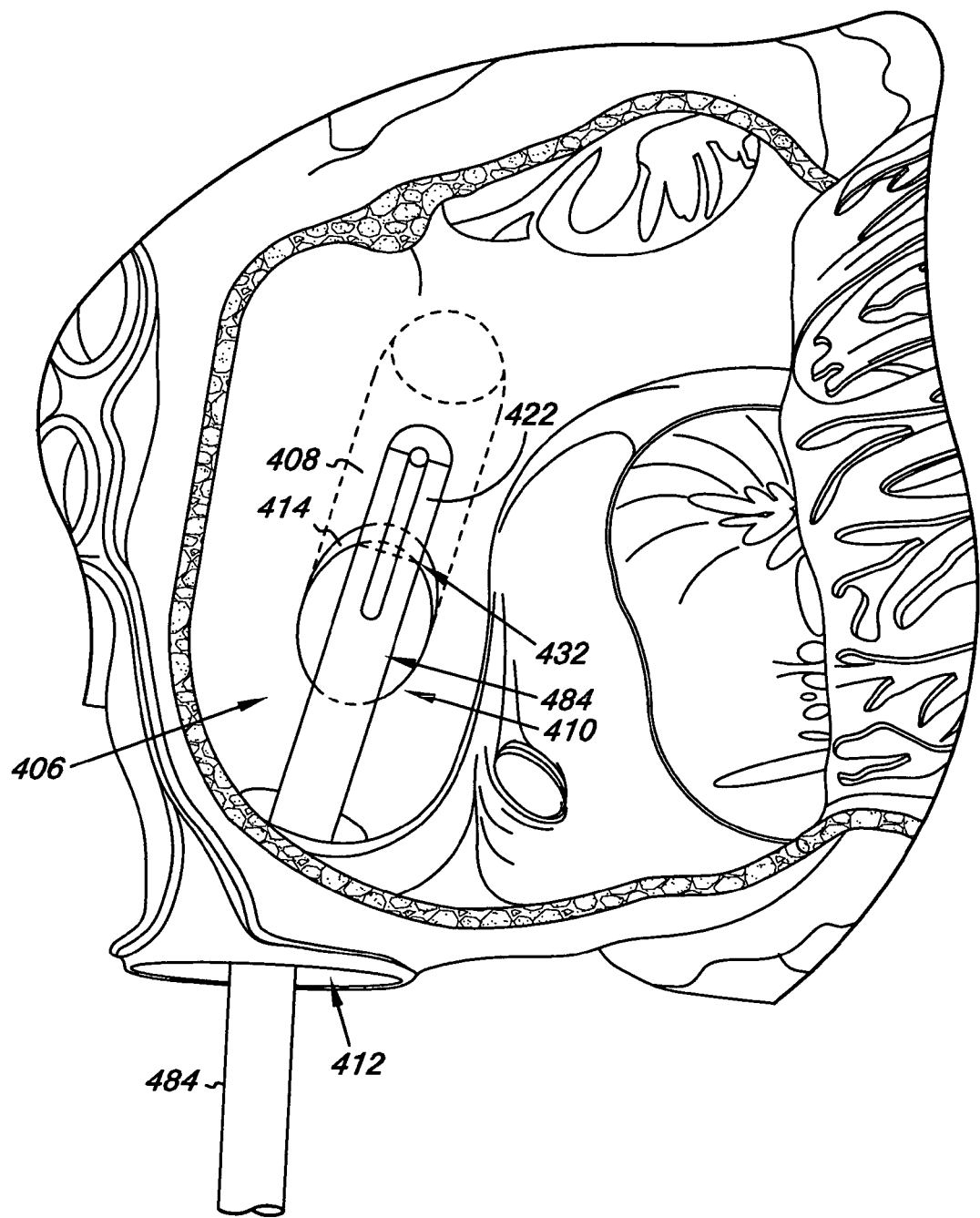
FIG. 4A illustrates a system of the present disclosure within the right atrium of the heart according to an embodiment of the present disclosure.
Figure 4B:
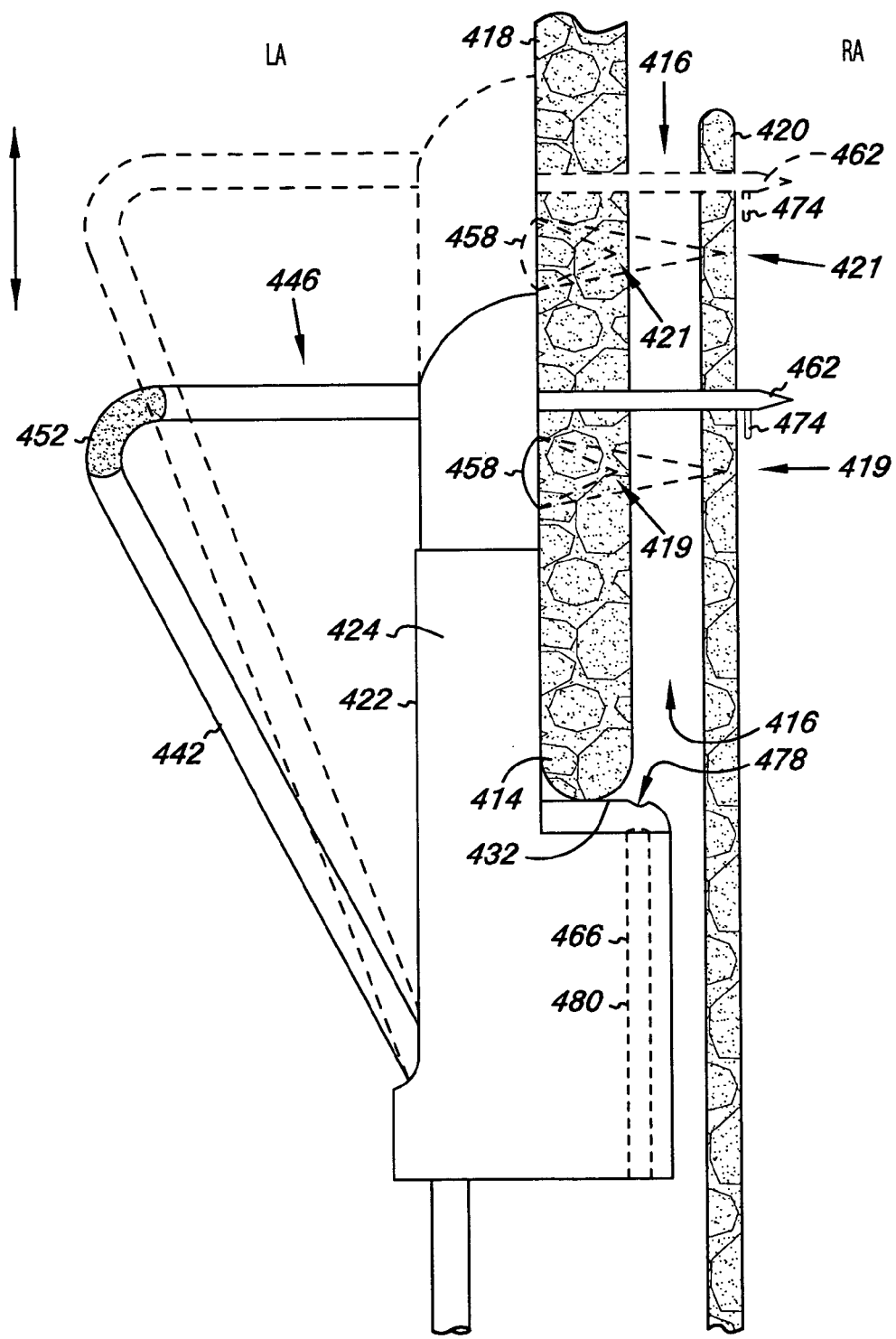
FIGS. 4B-4C illustrate the positioning device seated on the limbus of the septum secundum according to various embodiments of the present disclosure.
Figure 4C:
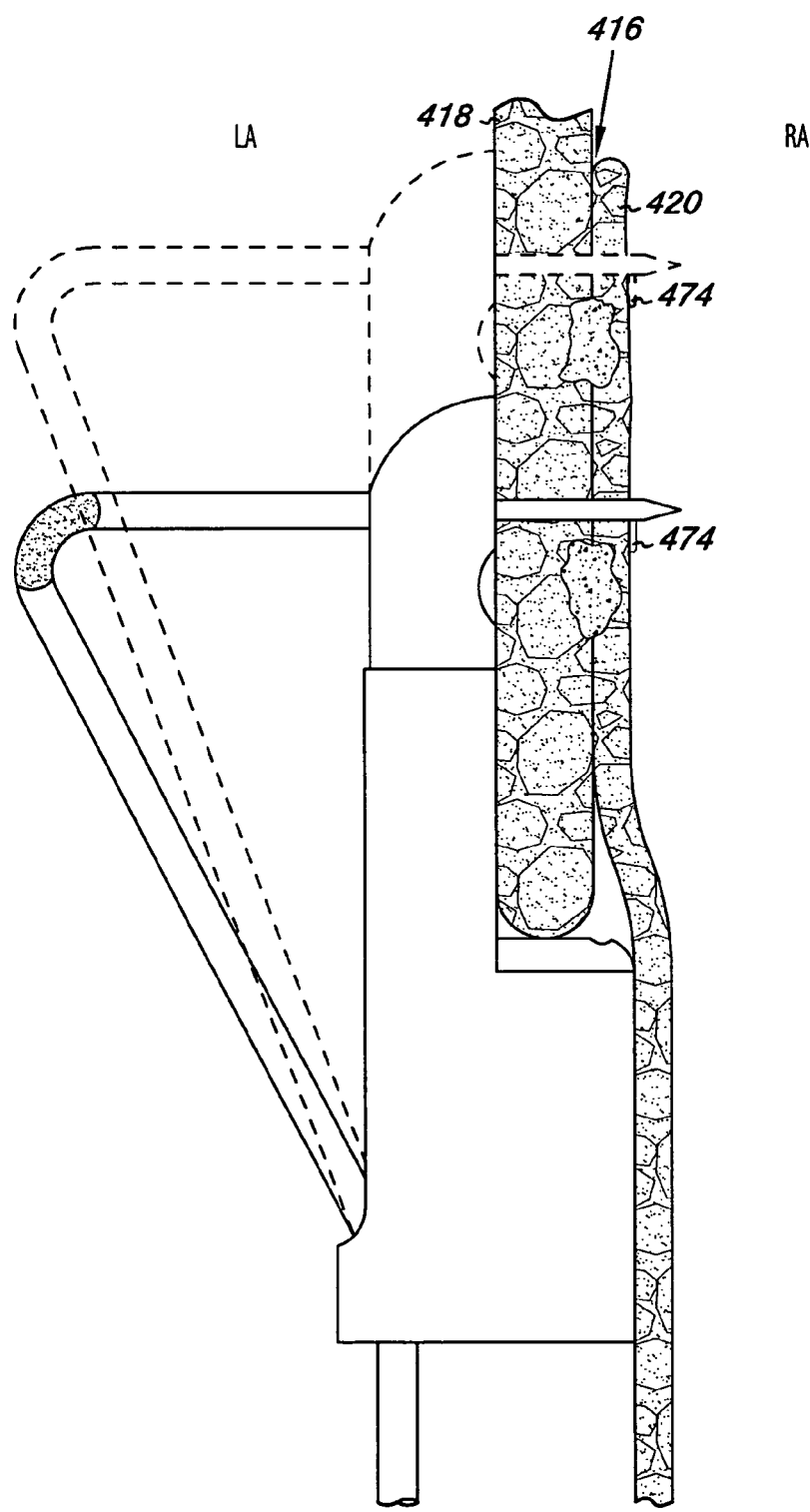

FIGS. 4A-4C illustrate embodiments of methods for bringing tissues of the passage (septum secundum and septum primum) together and fusing the tissues with an energy emitting device located within the human body.

Figure 4D:
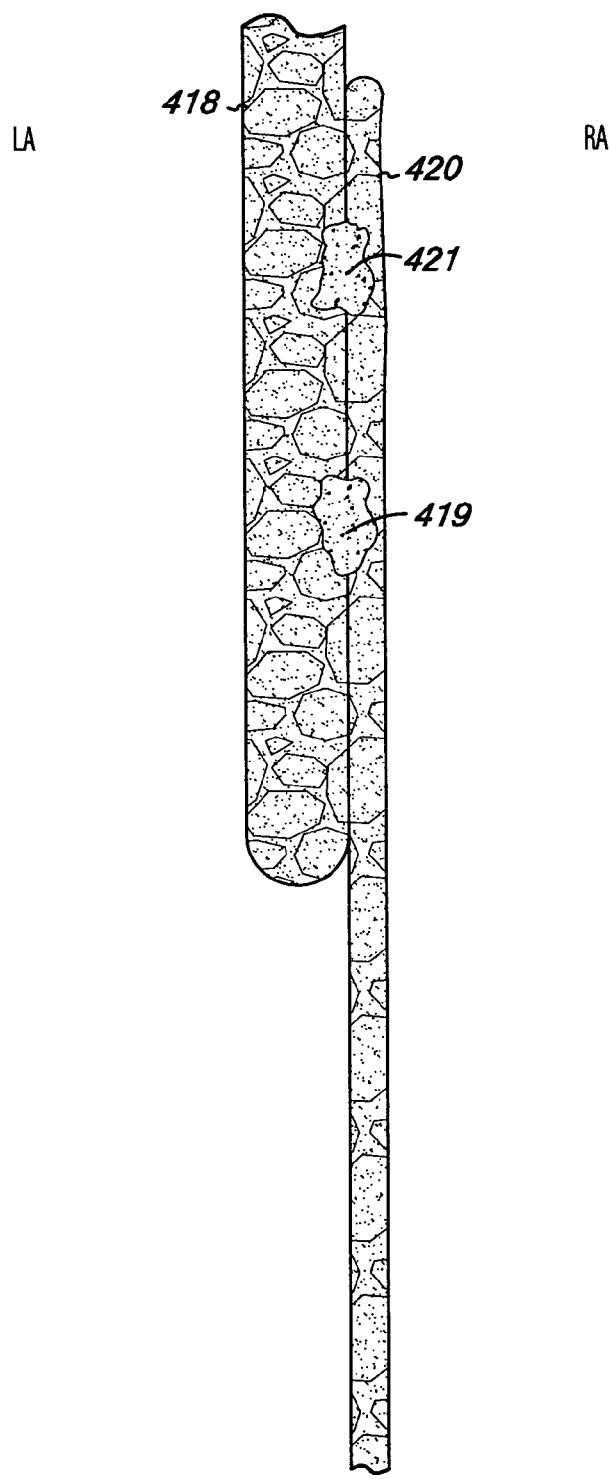
FIG. 4D illustrates an embodiment of a fused PFO.

FIG. 4A provides an illustration for accessing the right atrium of the heart according to the present disclosure. FIGS. 4B-4D provide illustrations for seating the occlusion device on the limbus of the septum secundum, apposing tissues of the passage together, and applying energy to the apposed tissue to fuse the tissue together.

In the embodiments illustrated in FIGS. 4B-5E, energy is applied to the tissues of the passage prior to bringing them together. However, as the reader will appreciate, applying energy to the tissues can be implemented prior to bringing the tissues together; while bringing the tissues together; and subsequent to bringing the tissues together.

Referring now to FIG. 4A, the method for occluding the PFO can include positioning the occlusion device 422 within the right atrium 402 by introducing the catheter 484 into the venous system of the patient using a minimally invasive percutaneous, transluminal catheter based delivery system.

A unique aspect of the fossa ovalis 410 is its location relative to the orifice of the inferior vena cava 412. Since the fossa ovalis 410 is located above and to the left of the orifice of the inferior vena cava 412, the occlusion device 422 can be deployed upon entering the right atrium 402 from the orifice of the inferior vena cava 412. For example, a guidewire can be positioned within the venous system and advanced to the right atrium 402 of a patient. In various embodiments, the right atrium 402 can be entered via the orifice of the inferior vena cava 412. The catheter 484, including the occlusion device 422, as described herein, can be positioned over the guidewire and the catheter advanced so as to position the distal end 490 of the catheter 484 at or adjacent the septal wall 406 of right atrium 402. Once positioned within the right atrium 402, the occlusion device 422 can be deployed from the catheter 484.

In various embodiments, radiopaque markers on the catheter 484 and/or the occlusion device 422 can be used to help positioning the occlusion device 422 within the right atrium 402 and/or to seat the occlusion device 422 on the limbus 414, as will be discussed herein. Radiopaue markers can also be placed on the various components of the occlusion device (e.g., tissue apposition members, pulling members, elongate structure) to help visualize and manipulate the components within the heart. In addition, orientation and visualization of the occlusion device 422 and the various components of the occlusion device may be accomplished through the use of any combination of MR imaging, echogenic, angioscopic, imaging ultrasound and fluoroscopic visualization techniques.

Seating the occlusion device 422 on the limbus 414 of the septum secundum 410 can include positioning the occlusion device 422 adjacent the limbus 414. To do this, the deployed occlusion device 422 can be positioned against the septal wall 406 and slid along the septal wall 406 of the right atrium toward the interatrial septum 408. Because the limbus 414 includes the pronounced anterosuperior margin of the fossa ovalis 410, the limbus 414 can catch the ledge of the occlusion device 422 as the occlusion device 422 slides along the septal wall 406 to seat the occlusion device on the limbus 414.

In various embodiments, seating the occlusion device on the limbus 414 of the septum secundum 418 can help to locate various components of the occlusion device in their proper positions relative to the passage 416 (i.e., PFO). For example, seating the occlusion device on the limbus 414 can help to properly locate the distal end 446 of the elongate structure 442 of the occlusion device 422 substantially perpendicular to the thick tissue 418, as shown in FIG. 4B. Positioning the elongate structure 442 can include pushing the elongate structure 442 away from the channel of the elongate body 424, as discussed herein. As the elongate structure 442 is pushed away from the channel, the flexible portion 452 forms the predetermined bend and the distal end 446 of the elongate structure 442 rotates along the rotation point from the first position to the second position, as described in connection with FIGS. 2A and 2B. Positioning the elongate structure 442 substantially perpendicular to the thick and thin tissue 418 and 420 can help to properly position tissue apposition member 462 perpendicularly relative to thick tissue 418 such that the tissue apposition member 462 can extend through the passage 416 at substantially a right angle relative to the thick and thin tissues 418 and 420 as shown in FIG. 4B.

In an alternative embodiment, a different tissue apposition member can be extended from the third lumen 476 of the occlusion device, as discussed herein. In this alternative embodiment, tissue apposition member (i.e., suction arm 480) can be extended from the third lumen 476 and away from the ledge 432 of the elongate body 424 through the second opening 478. In this embodiment, a vacuum force can be applied to the thick and the thin tissues 418 and 420 to bring them together.

In various embodiments, the method for occluding the PFO includes applying energy to tissues of the passage with the occlusion device to substantially occlude the PFO. In various embodiments, applying energy to tissues of the passage includes applying ultrasound focused to a high intensity to the tissues. For example, in various embodiments in FIG. 4B, energy emitting device 458 applies focused ultrasound at a high intensity to the thick and thin tissue 418 and 420 at a first location 419. In various embodiments, the beam of ultrasound can include a frequency in a range of 0.8-15.0 MHz, an intensity in a range of 1,000 Watt/cm$^2$, and a focus in the range of a 0.75 to 1.25 cm ellipse.

As discussed herein with respect to FIGS. 2A, 3A-3B, the energy emitting device 458 can be coupled to conductors, a signal generator, amplifier, program instructions executing on a computer, targeting device, etc. As one of ordinary skill will appreciate, the conductors can extend from the energy emitting device 458 through the catheter 484 and to, for example, a signal generator and amplifier, etc., to provide power to the energy emitting device 458 and to communicatively couple the occlusion device to various components, e.g., computer and/or targeting device.

In the embodiment shown in FIG. 4B, the HIFU is indicated by dotted lines originating from the HIFU transducer 458. As the HIFU approaches the on the thick and thin tissues, the HIFU narrows to a focal point at two targets indicated as a first location 419. At the focal point, the thick and thin tissues rapidly begin to heat and denature, as discussed herein. As the reader will appreciate, the position of the focal point relative to the HIFU transducer 458 is a function of the geometry of the HIFU transducer and thus, the focal point can depend, in part, on the location of the HIFU transducer relative to the two targets (i.e., first location 419). As the reader will appreciate, the HIFU transducer illustrated in FIG. 4B (i.e., located within the human body) will have a different focal point and thus, a different geometry than a HIFU transducer configured to apply HIFU to the first location 419 from outside the human body, as will be discussed herein.

In various embodiments in FIG. 4B, the energy emitting device 358 is focused on at the two targets indicated as the first location 419 which includes a portion of the thin tissue 420 and the thick tissue 418 just below the area of thick and thin tissue 418 and 420 through which the tissue apposition member 462 extends. As discussed herein, the HIFU denatures the tissue at and proximal to the target area (i.e., first area 419).

Referring now to FIGS. 4B and 4C, once the targeted tissues of the passage are denatured, the pulling member 474 can be extended from the tissue apposition member 462 to bring the tissues together. In order to bring the thick tissue 418 and the thin tissue 420 together, a pulling force can be applied to the proximal end of the pulling member 474. The pulling force causes the pulling member 474 to catch the thin tissue 420. Once caught, the thin tissue 420 can be pulled adjacent to the thick tissue 418, as shown in FIG. 4C. As discussed herein, once the tissues are denatured and brought together, the tissues begin to renature and fuse together as they cool. In various embodiments, the process can be repeated to fuse the tissue at a second location 421, as indicated by the dotted lines in FIG. 4B, and thus, occlude the passage 416 (i.e, PFO).

FIG. 4D illustrates an embodiment of renatured tissues of the septum secundum and septum primum. In various embodiments in FIG. 4D, the thick and thin tissue 418 and 420 of the passage 416 have cooled and are fused at the first and second locations 419 and 421. In various embodiments, if the operator determines that the PFO is sufficiently occluded, the catheter and the occlusion device can be extracted from the patient leaving nothing behind in the heart.

Figure 5A:
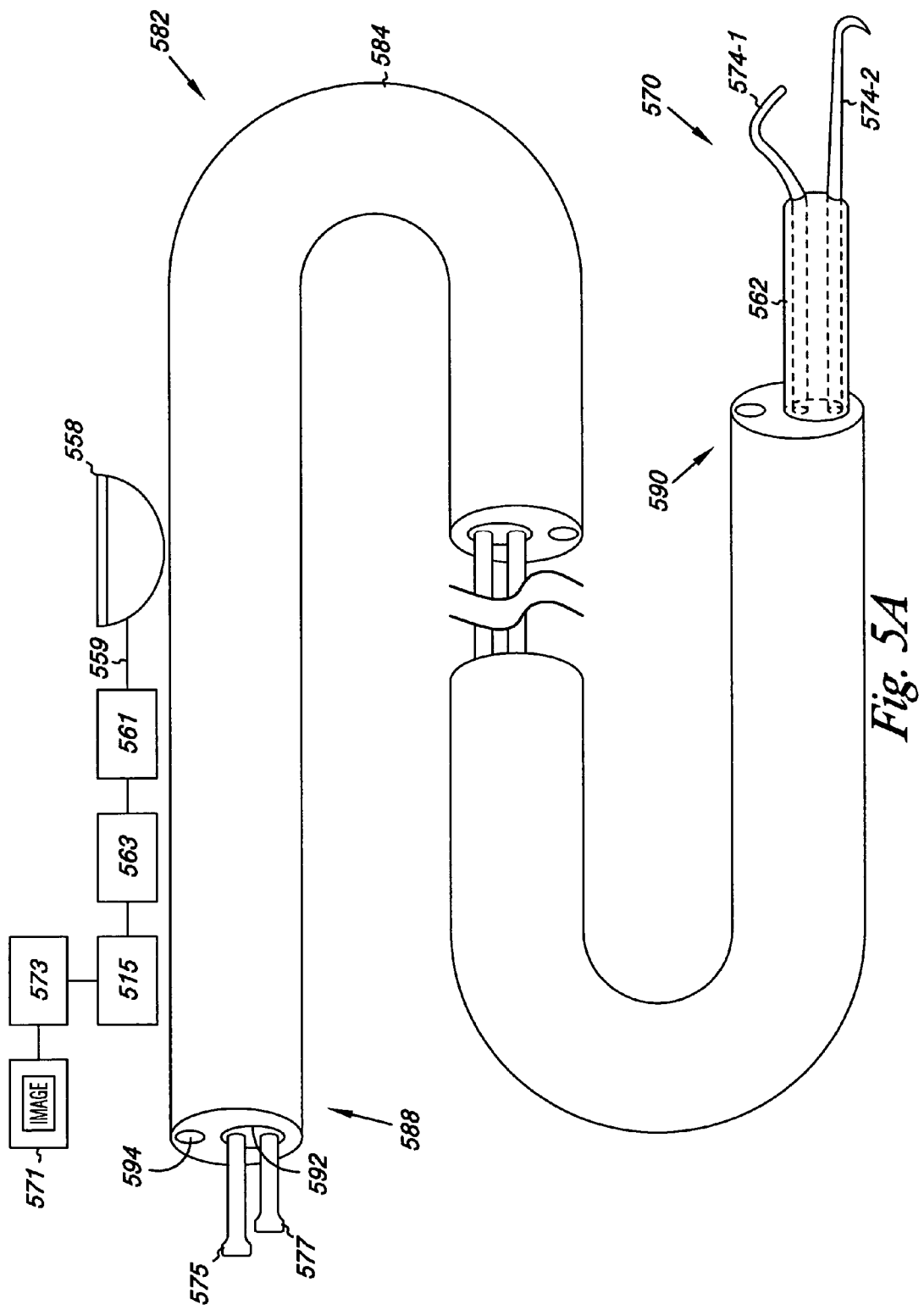
FIG. 5A illustrates an embodiment of a system of the present disclosure.

FIG. 5A illustrates another embodiment system 582 that includes a tissue apposition member 562 of the present disclosure. FIGS. 5B-5E illustrate embodiments of methods for bringing tissues of the passage together and fusing the tissues with an energy emitting device located outside the human body.

As shown in FIG. 5A, system 582 includes the tissue apposition member 562 illustrated in FIG. 2C. System also includes catheter 584 as discussed herein. In various embodiments, the tissue apposition member 562 can be positioned within lumen 592 of the catheter 584 and extend between the proximal end 588 and the distal end 590 of the catheter 584. In various embodiments, the catheter 584 including the tissue apposition member 562 therein, can be positioned proximal to or adjacent the passage using a variety of techniques. In various embodiments, the guidewire lumen 594 can receive a guidewire for positioning the catheter 584 and the tissue apposition member within the right atrium, as discussed herein.

The system 582 can also include the targeting device 515 and associated components to help position the catheter adjacent the passage. For example, in some embodiments, components of the targeting device 515 can include radiopaque markers on the catheter and/or the tissue apposition member can be used to help position the tissue apposition member within the right atrium and proximal to or adjacent the passage, as discussed herein. Radiopaue markers can also be placed on the various components of the occlusion device (e.g., tissue apposition members, pulling members, elongate structure) to help visualize and manipulate the components within the heart. In addition, orientation and visualization of the tissue apposition member and the pulling members may be accomplished through the use of any combination of MR imaging, echogenic, angioscopic, imaging ultrasound and fluoroscopic visualization techniques.

Figure 5B:
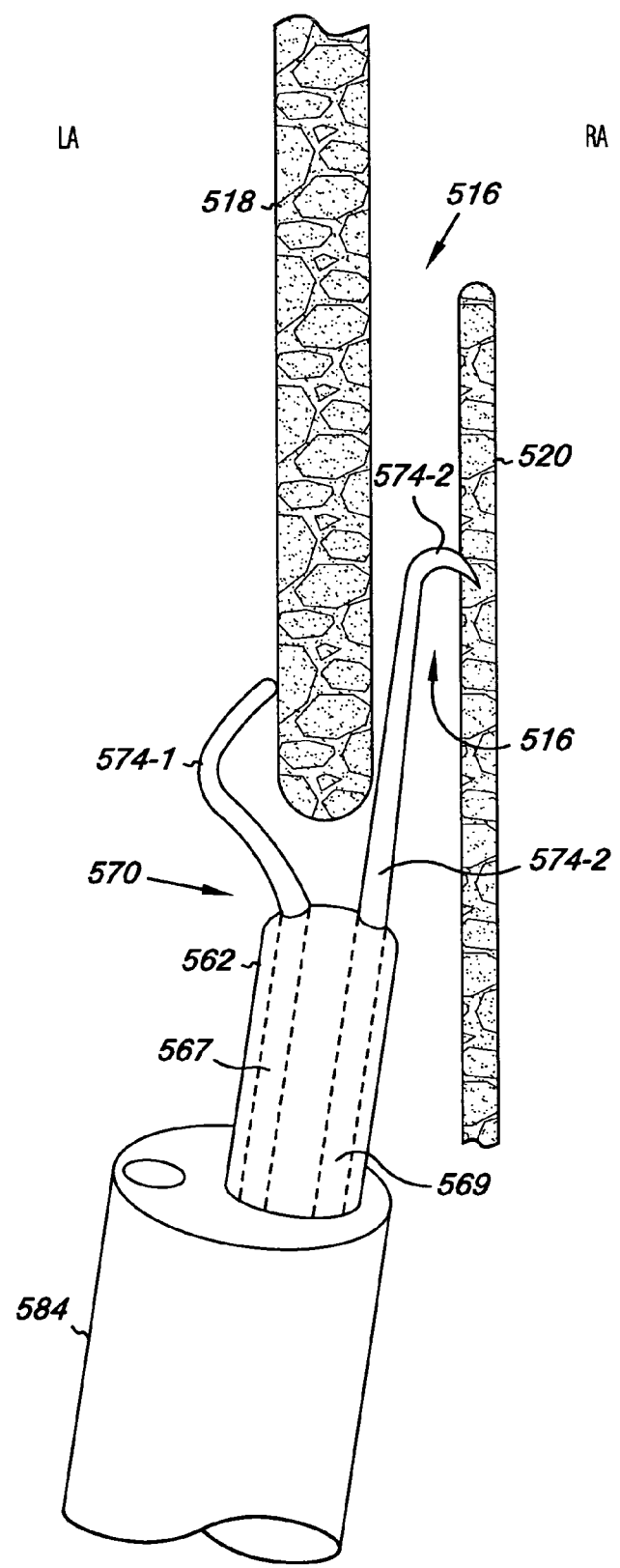
FIGS. 5B-5C illustrate an embodiment of a tissue apposition member of the present disclosure.

The embodiment of FIG. 5B illustrates in more detail an operation of the pulling members 574-1 and 574-2 extend between the proximal end 568 and the distal end 570 of the tissue apposition member 562. In various embodiments, a proximal end 575 of the first pulling member 574-1 and a proximal end 577 of the second pulling member 574-2 extend from lumen 592 of catheter 584 at the proximal end 588 of the catheter 584. As will be discussed herein, the proximal ends 575 and 577 can be manipulated by an operator to help position the first and second pulling members 574-1 and 574-2 adjacent tissues of the passage. In addition, the proximal ends 575 and 577 can be manipulated to help bring the tissues of the passage together.

System 582 can also include energy emitting device 558. As discussed herein in connection with FIGS. 3A-3B, the energy emitting device 558 can be operatively coupled to conductors 559, a signal generator 561, amplifier 563, a computer 573 including computer executable instructions (e.g., software), display 571, and the targeting device 515, etc. As discussed herein, the energy emitting device 558 can emit high intensity focused ultrasound (HIFU) to a target provided by the targeting device 515. In various embodiments, the system 582 can be used to target tissues of the passage, bring tissues of the passage together, and fuse the tissues so as to occlude the PFO, as illustrated in FIGS. 5B-5E.

In various embodiments in FIG. 5B, one method for bringing tissues of the passage together can include extending the distal end 570 of the tissue apposition member 562 from the catheter 584 and positioning the distal end 570 proximal to the opening in the passage 516 (i.e., the PFO).

Once positioned, first and second pulling members 574-1 and 574-2 can be extended from lumens 567 and 569 at distal end 570 of the tissue apposition member 562. As discussed herein, the pulling members 574-1 and 574-2 include the predefined shape designed to help position first and second pulling members 574-1 and 574-2 at predetermined locations relative to the passage when they are extended from the lumens 567 and 569. In various embodiments in FIG. 5B, the predefined shape of the first pulling member 574-1 is designed to be positioned adjacent the thick tissue 518 on the right atrial side of the passage 516 when it is extended from the lumen 567. In addition, the predefined shape of first pulling member 574-1 includes the predetermined bend designed to maintain the bend against the resistive force of the thick tissue 518 when the distal end of the first pulling member 574-1 is retracted into lumen 567. As used herein, the resistive force of the thick tissue 518 is a tendency of the thick tissue 518 to return to its original position prior to bringing the thick and the thin tissues together.

The second pulling member 574-2 also includes a predefined shape. The predefined shape of pulling member 574-2 can provide for the proper positioning of the second pulling member 574-2 within the passage when it is extended from the tissue apposition member 562. The predefined shape of the second pulling member 574-2 includes a substantially linear shape with a pointed tip at the distal end of second pulling member 574-2. The pointed tip can pierce the thin tissue of the passage when a portion of the second pulling member 574-2 is retracted lumen 569.

Figure 5C:
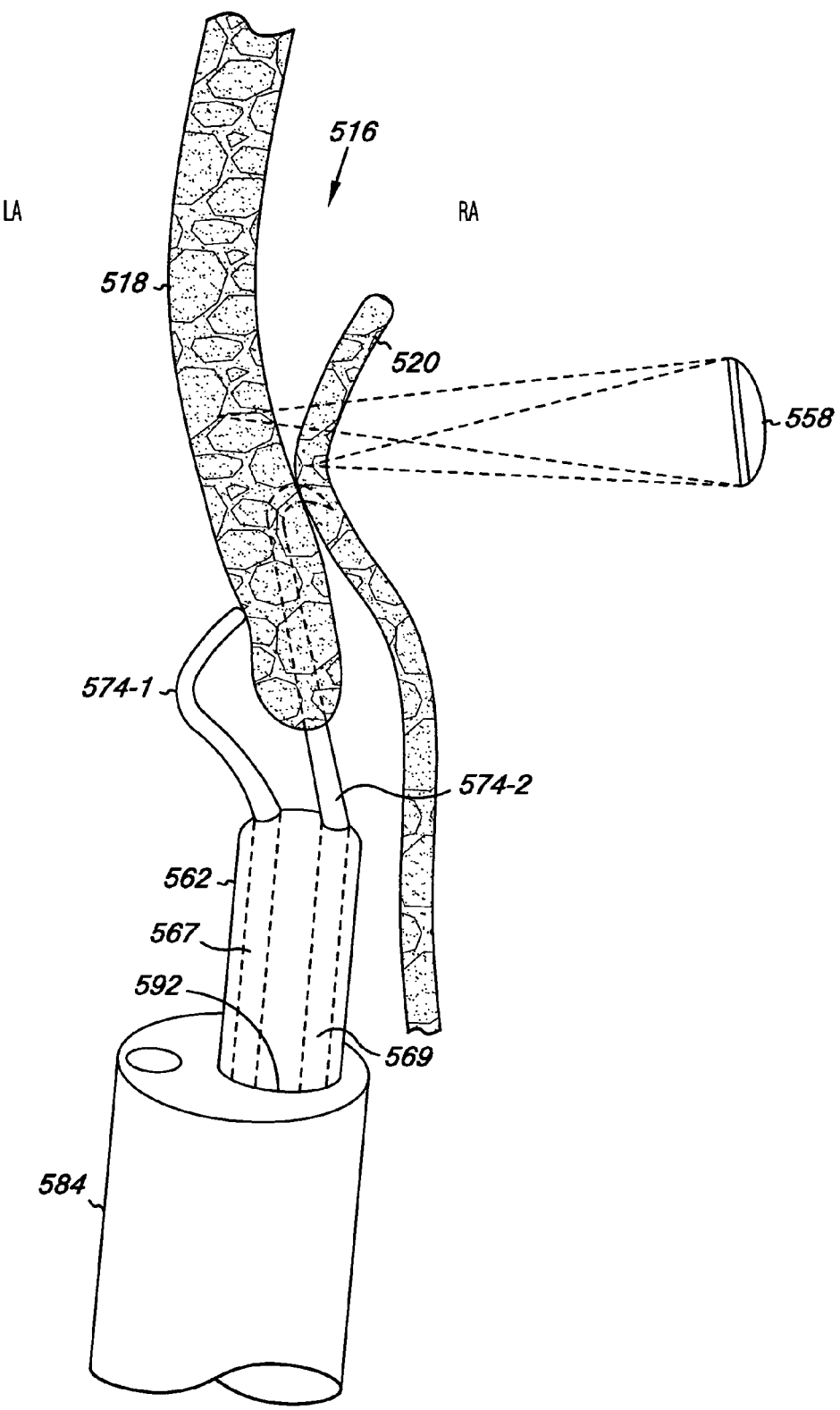

In various embodiments, the thick and thin tissue 518 and 520 can be brought together by manipulating the first and second pulling members 574-1 and 574-2. For example, an operator can apply a pulling force on the proximal ends of the pulling members 574-1 and 574-2 to partially retract a portion of the first and second pulling members 574-1 and 574-2 into their respective lumens 567 and 569, as shown in FIG. 5C. As the first pulling member 574-1 is retracting, the predefined shape of the first pulling member 574-1 helps to push the thick tissue toward the thin tissue, as shown in FIG. 5C. As the second pulling member is retracting, the pointed tip hooks the thin tissue 520 and pulls it downward toward the thick tissue 518, also shown in FIG. 5C.

In an alternative embodiment, the method for bringing the tissues together can include using a tissue apposition member having a suction arm that can apply a vacuum force to the tissues. For example, in various embodiments in FIG. 5D, the suction arm 580 can be extended from lumen 565 of the tissue apposition member 562 and positioned proximal the thick and thin tissue 518 and 520 and partially within the passage 516. In this embodiment, a vacuum force can be applied to the thick and thin tissues 520 and 518 to bring them together, as shown in FIG. 5D.

Figure 5D:
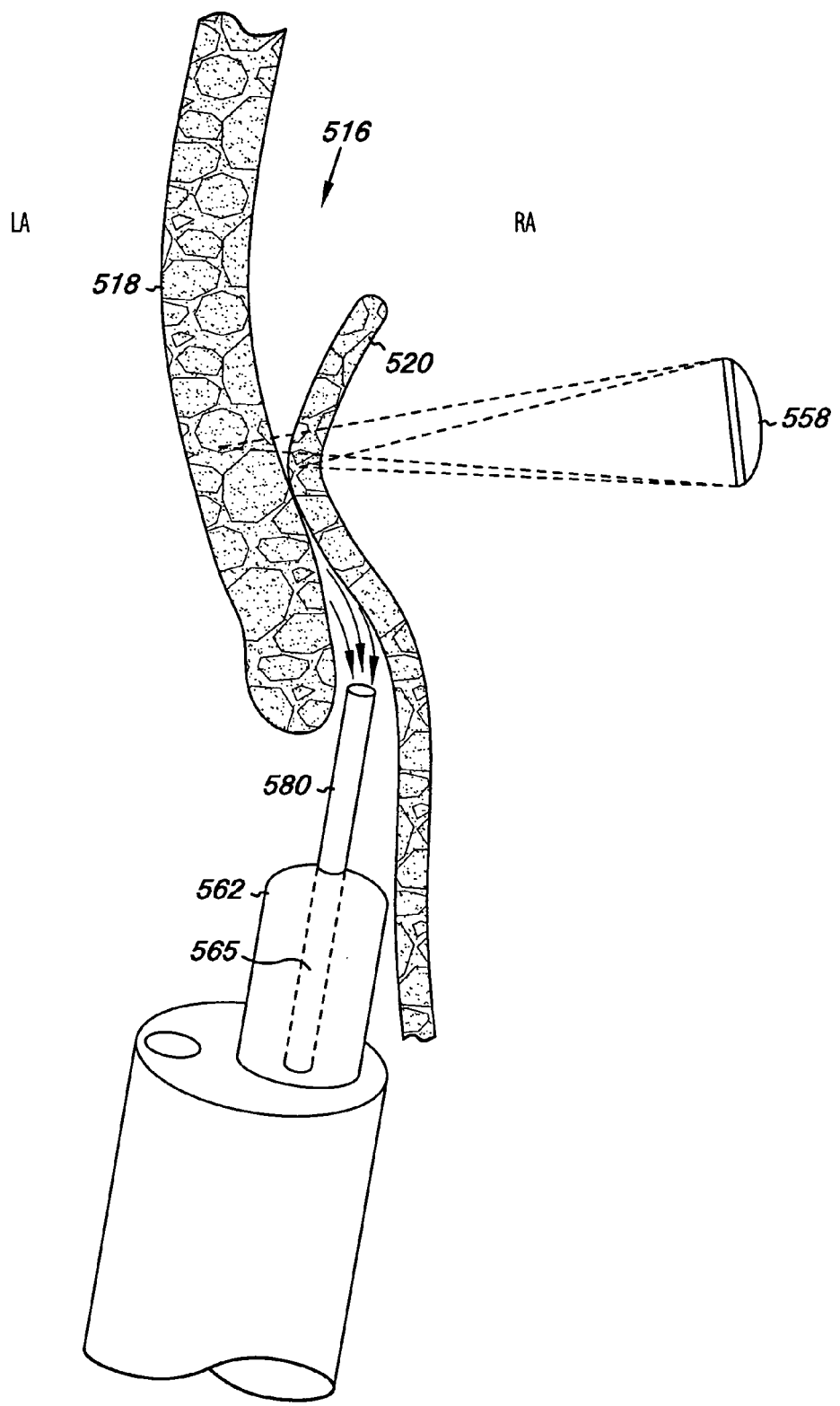
FIG. 5D illustrates another embodiment of a tissue apposition member of the present disclosure.
Figure 5E:
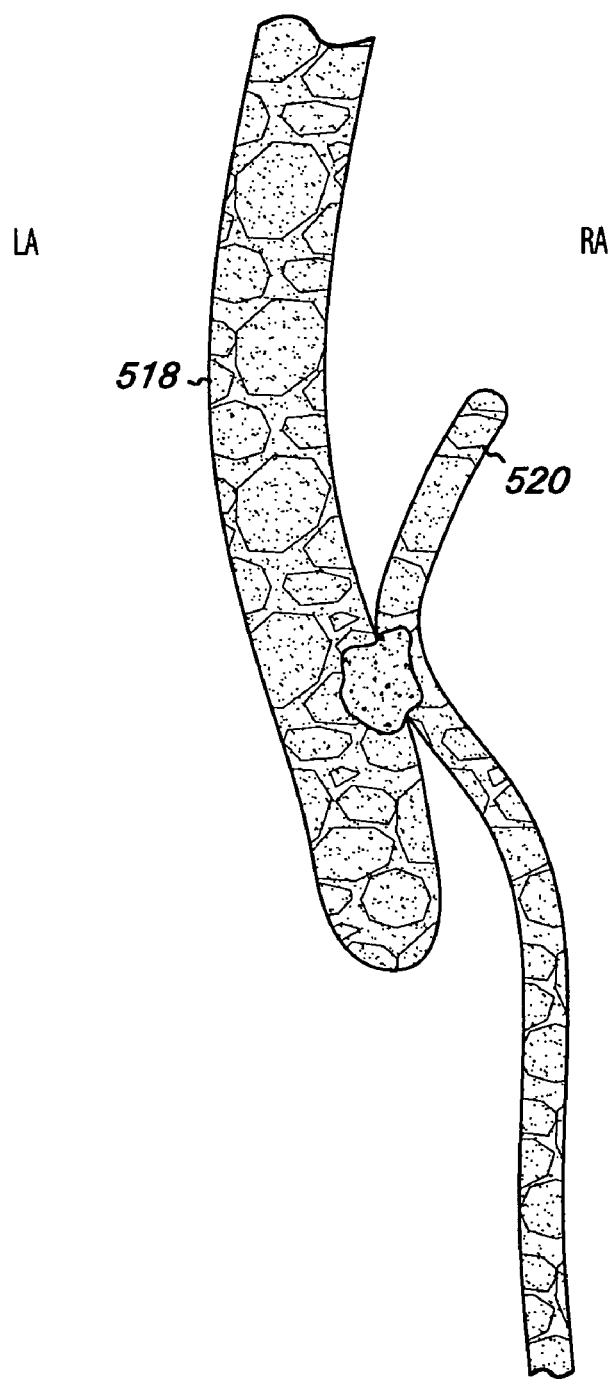
FIG. 5E illustrates another embodiment of a fused PFO.

In the embodiments of FIGS. 5C and 5D, energy can be applied to the tissues from outside the human body. In various embodiments, energy emitting device 558 positioned outside the body can emit HIFU to various targets on the thick and thin tissue 518 and 520. Once the targeted tissues of the passage are sufficiently denatured, the operator can deactivate the energy emitting device 558 and wait for the tissues to cool. As discussed herein, when the thick and thin tissues 518 and 520 have sufficiently cooled, they begin to renature and fuse together, as shown in FIG. 5E. As discussed herein, an operator of the targeting device 515 can monitor the thick and the thin tissues for changes (e.g., change in temperature) to determine if the tissues have sufficiently cooled and whether they have fused together. When the operator is satisfied that tissues are sufficiently cooled and fused together, the operator can remove the pulling members 574-1 and 574-2 by fully retracting them into their lumens 567 and 569 respectively. Because the second pulling member 574-2 hooks the thin tissue by partially retracting a portion of the second pulling member, the operator can first extend the second pulling member 574-2 to release the pointed tip from the tissue before retracting it. Once released, the second pulling member 574-2 can then be fully retracted into the tissue apposition member. In an alternative embodiment, the second pulling member 574-2 can be formed of a bioabsorbable material. In such an embodiment, the second pulling member can be released from the tissue apposition member 562 and left behind to degrade in the human body.

While the present disclosure has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An occlusion device, comprising:
   an elongate body having a first lumen and a wall, the first lumen extending from a proximal end toward a distal end of the elongate body and the wall extending from the distal end towards the proximal end to a ledge that extends away from the wall, the wall including a wall opening such that a second lumen extends from the wall opening completely through the elongate body, where the second lumen is transverse to the first lumen;
   an elongate structure having a lumen, the elongate structure extendably and rotatably positioned at least partially within the first lumen of the elongate body to pass through the first lumen to the second lumen;
   a tissue apposition member that is extendably positioned within the lumen of the elongate structure; and
   an energy emitting device extendably coupled to a portion of the elongate body proximal to the distal end of the elongate body.

2. The apparatus of claim 1, where the elongate body includes a surface defining a channel extending longitudinally between the first lumen and the second lumen.

3. The apparatus of claim 2, where the elongate structure includes a flexible portion along which the elongate structure bends under a compression force to push the elongate structure away from the channel of the elongate body.

4. The occlusion device of claim 2, where the elongate body includes a third lumen extending from the proximal end and toward the ledge of the elongate body.

5. The occlusion device of claim 4, including a suction arm that extends away from the ledge when extended from the third lumen.

6. The occlusion device of claim 1, where the elongate body includes an extendable portion proximal to the distal end of the elongate body.

7. The occlusion device of claim 1, where the tissue apposition member includes an elongate body having a lumen extending from a proximal end toward a distal end, the distal end including a piercing structure, and a pulling member extendably positioned within the lumen of the tissue apposition member.

8. A system for apposing tissues of a defective occlusion, comprising:
   a catheter including:
      a first elongate body having a catheter lumen; and
      an occlusion device extendably positioned within the catheter lumen of first the elongate body, the occlusion device having a first lumen and a wall, the first lumen extending from a proximal end toward a distal end of the occlusion device and the wall extending from the distal end towards the proximal end to a ledge that extends away from the wall, the wall including a wall opening such that a second lumen extends from the wall opening completely through the occlusion device, where the second lumen is transverse to the first lumen;
   a tissue apposition member extendably positioned within a lumen of a second elongate body;
   a targeting device configured to locate and guide focused ultrasound to a target including apposed tissues; and
   an energy emitting device configured to emit focused ultrasound at a high intensity to the target.

9. The system of claim 8, where the targeting device includes a magnetic resonance imaging device.

10. The system of claim 8, where the targeting device includes an imaging ultrasound device.

11. The system of claim 8, where the targeting device includes a monitoring functionality configured to monitor physical changes to the target induced by the focused ultrasound.

12. The system of claim 8, where the energy emitting device is configured to emit the focused ultrasound to the target from outside a human body.

13. The system of claim 8, where the energy emitting device is configured to emit the focused ultrasound to the target from within a human body.

14. The system of claim 8, where the energy emitting device configured to emit the focused ultrasound includes the targeting device.

15. The system of claim 8, where the tissue apposition member includes a pulling member extendably positioned within a lumen of the tissue apposition member.

16. The system of claim 15, where the pulling member includes a predefined shape configured to manipulate tissues of the defective occlusion.

* * * * *